United States Patent
Sato

(10) Patent No.: US 8,952,335 B2
(45) Date of Patent: Feb. 10, 2015

(54) RADIOLOGICAL IMAGE RADIOGRAPHING DEVICE, RADIATION IMAGE RADIOGRAPHING SYSTEM, AND RADIATION IMAGE RADIOGRAPHING METHOD

(75) Inventor: Keiichiro Sato, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 282 days.

(21) Appl. No.: 13/600,008

(22) Filed: Aug. 30, 2012

(65) Prior Publication Data

US 2013/0051525 A1 Feb. 28, 2013

(30) Foreign Application Priority Data

Aug. 31, 2011 (JP) ................. 2011-189930

(51) Int. Cl.
- *A61B 6/00* (2006.01)
- *G03B 42/02* (2006.01)
- *G01T 1/24* (2006.01)

(52) U.S. Cl.
USPC ............ 250/370.09; 250/370.08; 250/370.01; 250/214.1; 250/346; 250/370.11; 257/E31.117; 257/E31.119; 257/40; 257/444; 257/53; 378/101; 378/102; 378/116; 378/62; 378/91

(58) Field of Classification Search
USPC ......... 250/370.09, 370.01, 370.1, 397, 214.1, 250/346, 361 R, 370.11; 257/E31.117, 257/E31.119, E27.146, E27.132, 40, 444, 257/53, 72; 378/101, 102, 116, 62, 91, 378/98.8, 41, 63
See application file for complete search history.

(56) References Cited

U.S. PATENT DOCUMENTS

| | | | |
|---|---|---|---|
| 6,635,860 B2 * | 10/2003 | Sato et al. | 250/214.1 |
| 6,797,960 B1 * | 9/2004 | Spartiotis et al. | 250/370.09 |
| 6,885,005 B2 * | 4/2005 | Sato et al. | 250/370.01 |
| 7,109,491 B2 * | 9/2006 | Shinden | 250/370.09 |
| 7,365,337 B2 * | 4/2008 | Tsuchino et al. | 250/370.09 |
| 8,183,822 B2 * | 5/2012 | Tsubota et al. | 320/106 |
| 8,222,589 B2 * | 7/2012 | Wang | 250/214 R |

(Continued)

FOREIGN PATENT DOCUMENTS

| | | |
|---|---|---|
| JP | 2009-219538 | 10/2009 |
| JP | 2010-264085 A | 11/2010 |
| JP | 2010-268171 A | 11/2010 |

OTHER PUBLICATIONS

Notice of Reasons for Rejection issued by JPO on Aug. 26, 2014 in connection with corresponding Japanese Patent Appln. No. JP-2011-189930.

*Primary Examiner* — David A Vanore
(74) *Attorney, Agent, or Firm* — Jean C. Edwards, Esq.; Edwards Neils PLLC

(57) ABSTRACT

Bias lines are provided for respective columns of pixels, and of a plurality of bias lines, bias lines provided at an interval of 10 mm are connected to a bias power source through a current detector. The remaining bias lines are connected directly to the bias power source without passing through the current detector. In each pixel, if electric charge is generated by a radiation detection element in accordance with the dose of irradiated radiation, a current flows in the bias line in accordance with the generated electric charge. The current detector detects the current flowing in the bias line, and a control unit detects, as the timing of starting irradiation of a radiation, when the detected current (current value) is equal to or greater than a threshold value, and starts radiographing of a radiological image.

17 Claims, 15 Drawing Sheets

(56) References Cited

U.S. PATENT DOCUMENTS

| | | | |
|---|---|---|---|
| 8,358,740 B2* | 1/2013 | Nakatsugawa et al. | 378/116 |
| 8,471,213 B2* | 6/2013 | Yagi et al. | 250/370.09 |
| 8,513,609 B2* | 8/2013 | Tsubota et al. | 250/349 |
| 8,642,970 B2* | 2/2014 | Iwakiri et al. | 250/370.08 |
| 8,798,235 B2* | 8/2014 | Ohta et al. | 378/102 |
| 8,798,236 B2* | 8/2014 | Ohta et al. | 378/102 |
| 2010/0148081 A1* | 6/2010 | Yoshimi et al. | 250/370.08 |
| 2010/0207032 A1* | 8/2010 | Tsubota et al. | 250/370.09 |
| 2011/0170669 A1* | 7/2011 | Nakatsugawa et al. | 378/116 |
| 2011/0233411 A1* | 9/2011 | Nishino et al. | 250/361 R |
| 2012/0132820 A1* | 5/2012 | Iwakiri et al. | 250/370.08 |
| 2013/0083892 A1* | 4/2013 | Ohta et al. | 378/62 |
| 2013/0114793 A1* | 5/2013 | Ohta et al. | 378/63 |
| 2013/0126850 A1* | 5/2013 | Iwakiri et al. | 257/40 |
| 2014/0086391 A1* | 3/2014 | Ohta et al. | 378/91 |
| 2014/0110595 A1* | 4/2014 | Iwakiri et al. | 250/394 |
| 2014/0161228 A1* | 6/2014 | Kitano et al. | 378/62 |
| 2014/0169650 A1* | 6/2014 | Sakimoto et al. | 382/131 |

* cited by examiner

RADIOLOGICAL IMAGE RADIOGRAPHING DEVICE, RADIATION IMAGE RADIOGRAPHING SYSTEM, AND RADIATION IMAGE RADIOGRAPHING METHOD

CROSS-REFERENCE TO RELATED APPLICATIONS

This application claims priority from Japanese Patent Application No. 2011-189930, filed Aug. 31, 2011, the contents of which are hereby incorporated by reference in their entirety.

BACKGROUND OF THE INVENTION

1. Field of the Invention

The present invention relates to a radiological image radiographing device, a radiological image radiographing system, and a radiological image radiographing method, and in particular, to a radiological image radiographing device, a radiological image radiographing system, and a radiological image radiographing method which are used when radiographing a radiological image according to an irradiated radiation.

2. Description of the Related Art

A radiological image radiographing device which performs radiography for the purpose of medical diagnosis or the like has hitherto become known. The radiological image radiographing device detects a radiation, which is irradiated from an irradiation device and transmits a subject, to radiograph a radiological image. The radiological image radiographing device collects and reads electric charge generated in accordance with an irradiated radiation to perform radiographing of a radiological image. As this kind of radiological image radiographing device, an FPD (Flat Panel Detector) panel, such as a so-called cassette, is used.

As this kind of radiological image radiographing device, a device including a radiation detection element, such as a photoelectric conversion element, which generates electric charge in accordance with a radiation detected when a radiation or light converted from a radiation is irradiated, a switch element which reads the electric charge generated by the radiation detection element, and a detection unit which detects the irradiation (the start or stop of irradiation) of the radiation based on the electric charge read from the switch element is known.

For example, JP2010-268171A describes a radiological image radiographing device which detects a current flowing in a bias line and detects the start of irradiation of a radiation based on the value of the detected current. For example, JP2010-264085A describes a radiological image radiographing device which detects a current flowing in a bias line, constantly performs integration processing on the detected current value, and determines whether or not the exposure of a radiation has started from the amount of change in the integrated value.

SUMMARY OF THE PRESENT INVENTION

As described above, in the technique which detects a current flowing in a bias line and detects the irradiation of the radiation based on the detected current, the current flowing in the bias line is detected by current detection means connected to the bias line. Since the current detection means is a load (resistance), a bias voltage may fluctuate when a current (electric charge) flows, and the bias voltage is likely to fluctuate. In general, while a photodiode or the like is used as the radiation detection element, since the dark current or gain of the photodiode fluctuates with the fluctuation in the bias voltage, offset and sensitivity may fluctuate. For this reason, there is a problem in that image irregularity or the like occurs in a radiographed radiological image, causing degradation of image quality.

The present invention has been made in view of the above-mentioned problems and an object of the present invention is to provide a radiological image radiographing device, a radiological image radiographing system, and a radiological image radiographing method capable of suppressing degradation of image quality.

In order to attain the above-described object, an aspect of the present invention provides a radiological image radiographing device. The radiological image radiographing device includes a plurality of pixels arranged in a matrix, each pixel having a radiation detection element which generates electric charge according to the dose of irradiated radiation and a switch element which reads the electric charge generated by the radiation detection element and outputs the electric charge to a signal line, a plurality of bias lines which supply a bias voltage applied from a bias power source to the radiation detection elements of the plurality of pixels, and an irradiation detection unit which detects a current flowing in some bias lines from among the plurality of bias lines and detects the irradiation state of the radiation based on change in the detected current.

Another aspect of the present invention provides a radiological image radiographing device. The radiological image radiographing device includes a plurality of pixels arranged in a matrix, each pixel having a radiation detection element which generates electric charge according to the dose of irradiated radiation and a switch element which reads the electric charge generated by the radiation detection element and outputs the electric charge to a signal line, a plurality of bias lines which supply a bias voltage applied from a bias power source to the radiation detection elements of the plurality of pixels, and an irradiation detection unit which stores electric charge flowing in some bias lines from among the plurality of bias lines for a preset time and detects the irradiation state of the radiation based on change in the amount of stored electric charge.

A further aspect of the present invention provides a radiological image radiographing device. The radiological image radiographing device includes a plurality of pixels arranged in a matrix, each pixel having a radiation detection element which generates electric charge according to the dose of irradiated radiation and a switch element which reads the electric charge generated by the radiation detection element and outputs the electric charge to a signal line, a plurality of bias lines which supply a bias voltage applied from a bias power source to the radiation detection elements of the plurality of pixels, and an irradiation detection unit which detects a voltage on some bias lines from among the plurality of bias lines and detects the irradiation state of the radiation based on change in the detected voltage.

At least one pixel adjacent to a pixel connected to a bias line which is used when detecting the irradiation of the radiation using the irradiation detection unit is connected to a bias line which is not used when detecting the irradiation of the radiation.

The number of bias lines which are used when detecting the irradiation of the radiation using the irradiation detection unit is equal to or smaller than the number of bias lines which are not used when detecting the irradiation of the radiation.

Bias lines which are used when detecting the irradiation of the radiation using the irradiation detection unit are provided at an interval equal to or smaller than the width of the irradiation field of the radiation to be irradiated.

The radiological image radiographing device further includes a complement unit which acquires image information according to the electric charge output from each of the plurality of pixels to the signal line for each pixel, and complements image information of a pixel connected to a bias line which is used when detecting the irradiation of the radiation using the irradiation detection unit with image information of a pixel adjacent to the pixel and connected to a bias line which is not used when detecting the irradiation of the radiation.

The radiological image radiographing device further includes an acquisition unit which collectively acquires image information according to the electric charge output from a pixel connected to a bias line, which is used when detecting the irradiation of the radiation using the irradiation detection unit, to the signal line and image information according to the electric charge output from a pixel connected to a bias line, which is not used when detecting the irradiation of the radiation, to the signal line.

The bias lines are provided for the respective rows or columns of the pixels.

Still another aspect of the present invention provides a radiological image radiographing system. The radiological image radiographing system includes an irradiation device, and the above-described radiological image radiographing device which radiographs a radiological image with a radiation irradiated from the irradiation device.

Yet another aspect of the present invention provides a radiological image radiographing method. The radiological image radiographing method includes, when radiographing a radiological image using a radiological image radiographing device including a plurality of pixels arranged in a matrix, each pixel having a radiation detection element which generates electric charge according to the dose of irradiated radiation and a switch element which reads the electric charge generated by the radiation detection element and outputs the electric charge to a signal line, and a plurality of bias lines which supply a bias voltage applied from a bias power source to the radiation detection elements of the plurality of pixels, detecting a current flowing in some bias lines from among a plurality of bias lines, detecting the irradiation state of a radiation based on change in the detected current, and controlling radiographing of the radiological image based on the detected irradiation state.

A further aspect of the present invention provides a radiological image radiographing method. The radiological image radiographing method includes, when radiographing a radiological image using a radiological image radiographing device including a plurality of pixels arranged in a matrix, each pixel having a radiation detection element which generates electric charge according to the dose of irradiated radiation and a switch element which reads the electric charge generated by the radiation detection element and outputs the electric charge to a signal line, a plurality of bias lines which supply a bias voltage applied from a bias power source to the radiation detection elements of the plurality of pixels, storing electric charge flowing in some bias lines from among a plurality of bias lines for a preset time, detecting the irradiation state of a radiation based on change in the amount of stored electric charge, and controlling radiographing of the radiological image based on the detected irradiation state.

Still another aspect of the present invention provides a radiological image radiographing method. The radiological image radiographing method includes, when radiographing a radiological image using a radiological image radiographing device including a plurality of pixels arranged in a matrix, each pixel having a radiation detection element which generates electric charge according to the dose of irradiated radiation and a switch element which reads the electric charge generated by the radiation detection element and outputs the electric charge to a signal line, a plurality of bias lines which supply a bias voltage applied from a bias power source to the radiation detection elements of the plurality of pixels, detecting a voltage on some bias lines from among a plurality of bias lines, detecting the irradiation state of a radiation based on change in the detected voltage, and controlling radiographing of the radiological image based on the detected irradiation state.

As described above, it is possible to provide the effect of suppressing degradation of image quality.

DESCRIPTION OF THE PREFERRED EMBODIMENTS

Hereinafter, an example of this embodiment will be described with reference to the drawings.

First Embodiment

Figure 1:
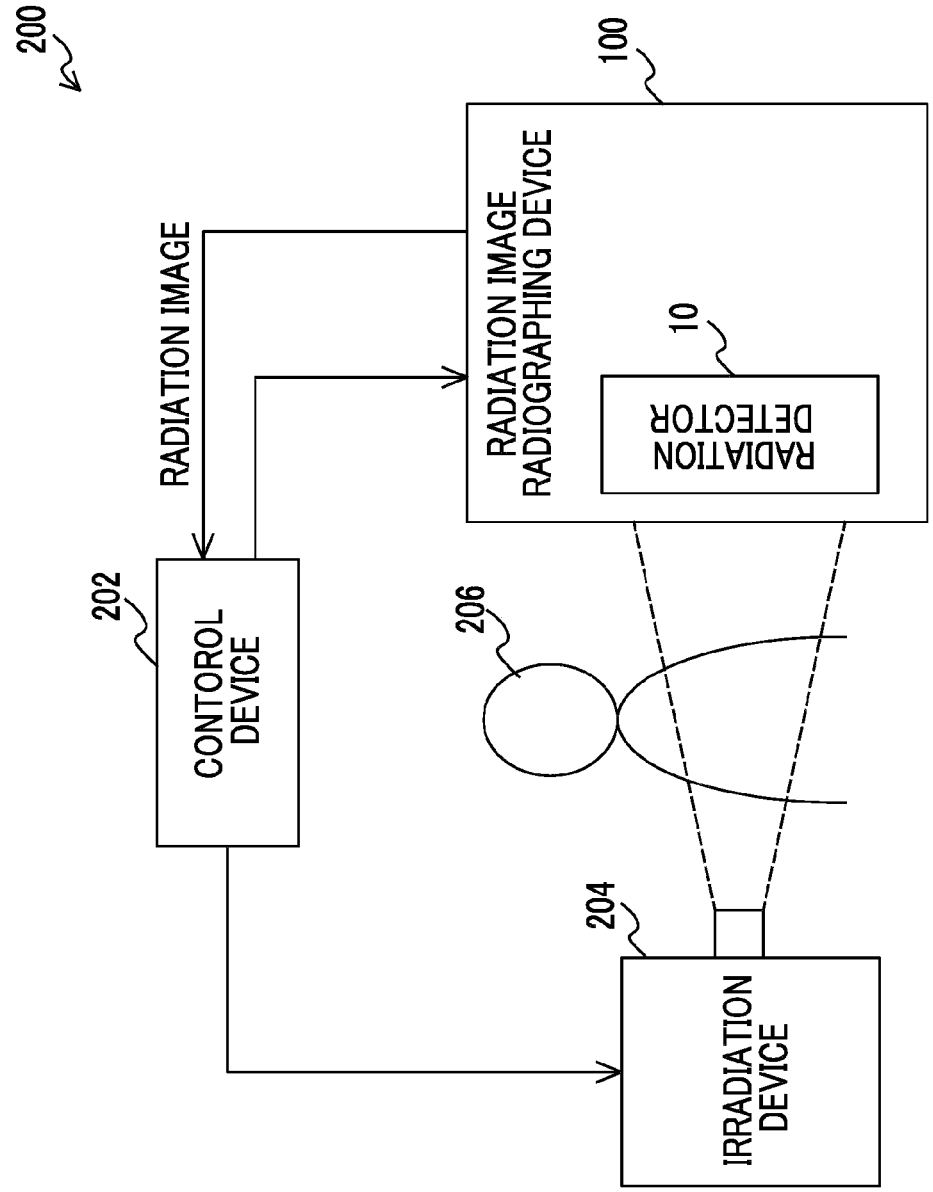
FIG. 1 is a schematic configuration diagram showing the schematic configuration of an example of a radiological image radiographing system according to a first embodiment.

First, the schematic configuration of a radiological image radiographing system using a radiological image radiographing device of this embodiment will be described. FIG. 1 is a schematic configuration diagram of an example of a radiological image radiographing system of this embodiment.

A radiological image radiographing system 200 includes an irradiation device 204 which irradiates a radiation (for example, X-ray or the like) onto a subject 206, a radiological image radiographing device 100 including a radiation detector 10 which detects the radiation irradiated from the irradiation device 204 and transmitting the subject 206, and a control device 202 which instructs radiographing of a radiological image and acquires the radiological image from the radiological image radiographing device 100. The radiation which has image information carried thereon after being irradiated from the irradiation device 204 and transmitting the subject 206 at a radiographing position is irradiated onto the radiological image radiographing device 100 at the timing under the control of the control device 202.

Figure 2:
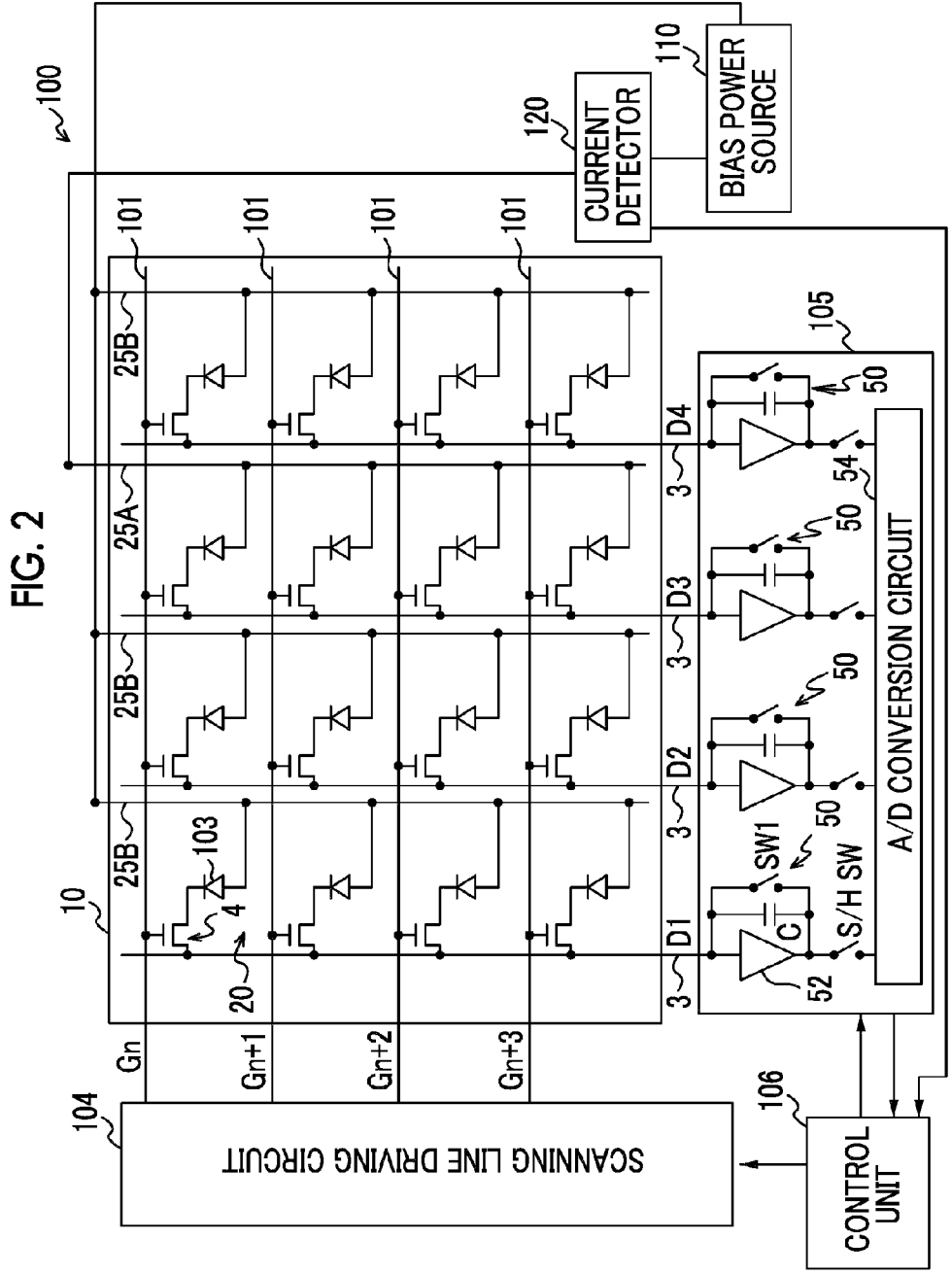
FIG. 2 is a configuration diagram showing an example of the overall configuration of the radiological image radiographing device according to the first embodiment.

Next, the schematic configuration of the radiological image radiographing device 100 of this embodiment will be described. In this embodiment, description will be provided as to a case where the present invention is applied to an indirect conversion-type radiation detector 10 which temporarily converts a radiation, such as X-ray, to light and converts the converted light to electric charge. In this embodiment, the radiological image radiographing device 100 includes an indirect conversion-type radiation detector 10. In FIG. 2, a scintillator which converts a radiation to light is not shown.

The radiation detector 10 has a plurality of pixels 20 arranged in a matrix, each pixel including a radiation detection element 103 which receives light to generate electric charge, and stores the generated electric charge and a TFT switch 4 which is a switch element for reading the electric charge stored in the radiation detection element 103. In this embodiment, light converted by a scintillator is irradiated, and electric charge is generated by the radiation detection element 103.

A plurality of pixels 20 are arranged in a matrix in one direction (the horizontal direction of FIG. 2, and hereinafter, referred to as "row direction") and a cross direction (the vertical direction of FIG. 2, and hereinafter, referred to as "column direction") with respect to the row direction. Although in FIG. 2, the arrangement of the pixels 20 is shown in a simplified form, for example, 1024 pixels 20 are arranged in each of the row direction and the column direction.

Figure 3:
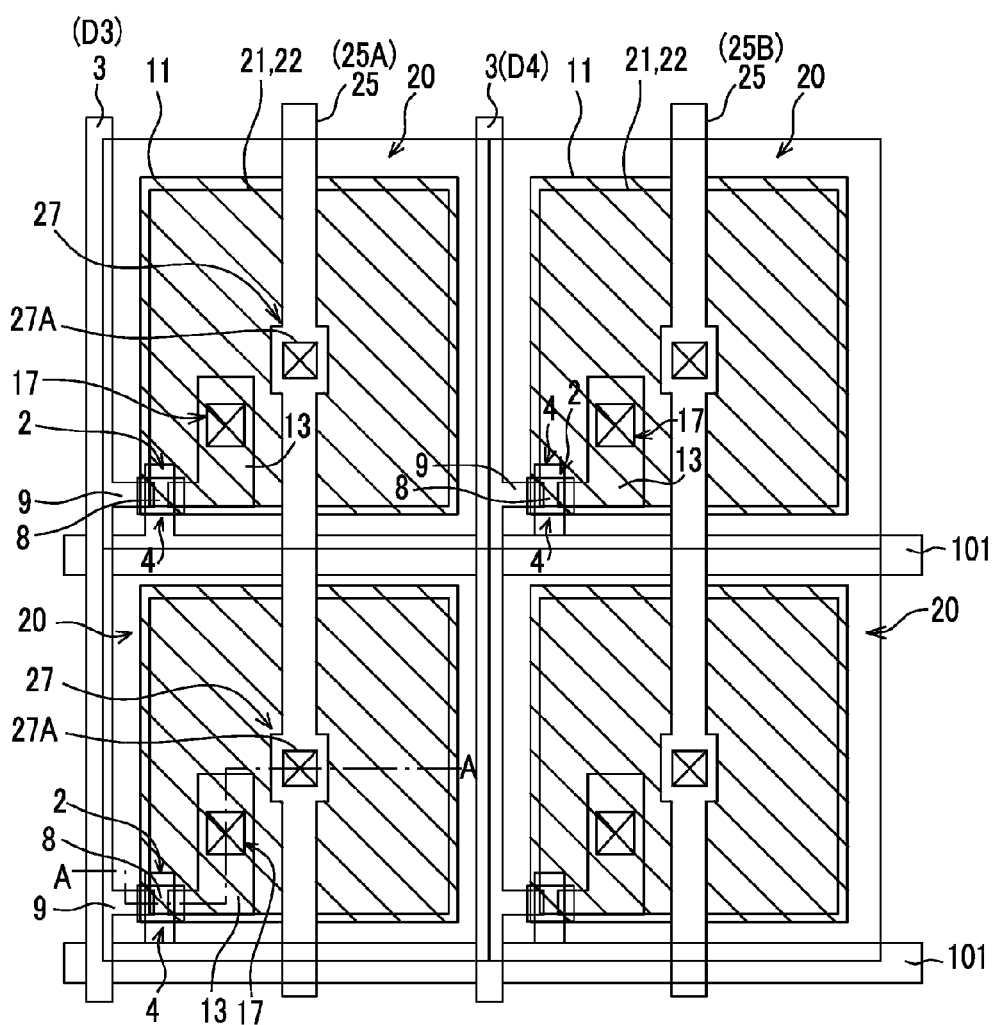
FIG. 3 is a plan view showing an example of the configuration of a radiation detector according to the first embodiment.

In the radiation detector 10, a plurality of scanning lines 101 for turning on/off the TFT switches 4 and a plurality of signal lines 3 for reading the electric charge stored in the radiation detection elements 103 are provided to cross each other on a substrate 1 (see FIG. 3). In this embodiment, the signal lines 3 are provided corresponding to the pixel arrays in one direction, and the scanning lines 101 are provided corresponding to the pixel arrays in the cross direction. For example, when 1024×1024 pixels 20 are arranged in the row direction and the column direction, 1024 signal lines 3 and 1024 scanning lines 101 are provided.

In the radiation detector 10, bias lines 25 (25A and 25B) are provided in parallel to the signal lines 3. In this embodiment, of a plurality of bias lines 25, some bias lines 25 (25A) are connected to a bias power source 110 through a current detector 120. The remaining bias lines 25 (25B) are connected directly to the bias power source 110 without passing through the current detector 120.

In this embodiment, the radiation detector 10 has the bias lines 25A at an interval of 10 mm. As a specific example, when the pixel region of the radiation detector 10 is formed to have a size of 14 inches (35.6 cm) in the row direction and 17 inches (43.2 cm) in the column direction, and the size of each of the pixels 20 is about 150 μm×150 μm, one line in 60 to 70 lines from among the bias lines 25 is the bias line 25A, and the remaining lines are the bias lines 25B. In this way, for how many bias lines 25 one bias line 25A is provided is determined depending on the size of each of the pixels 20.

In this embodiment, as described above, the bias lines 25A are provided at an interval of 10 mm in accordance with the irradiation region of a radiation in the radiological image radiographing device 100. In this embodiment, the irradiation region (irradiation field) of the radiation in the radiological image radiographing device 100 is about a finger of the subject 206 at the minimum, about 10 mm. For this reason, the bias lines 25A are provided at an interval of 10 mm, and at least one bias line 25A is provided for one irradiation region (irradiation field). In this way, at least one bias line 25A is provided for each irradiation region, thereby improving detection accuracy of the irradiation of the radiation. When the irradiation region (irradiation field) is different from 10 mm, the bias lines 25A may be provided at an interval equal to or smaller than the width (the width in the column direction) of the irradiation field such that at least one bias line 25A is provided in the irradiation region (irradiation field) at an interval according to the irradiation region.

The radiation detection element 103 of each of the pixels 20 is connected to the bias line 25 (25A or 25B) for each column of the pixels 20, and a bias voltage is applied from the bias power source 110 to the radiation detection element 103 through the bias line 25.

A driving signal for switching (driving) each TFT switch 4 flows in each scanning line 101. In this way, the driving signal flows in each scanning line 101 to switch each TFT switch 4.

An electrical signal according to electric charge stored in each pixel 20 flows in each signal line 3 in accordance with the switching state of the TFT switch 4 of each pixel 20. Specifically, an electrical signal according to the amount of electric charge stored when the TFT switch 4 of any one of the pixels 20 connected to each signal line 3 flows in each signal line 3.

A signal detection circuit 105 which detects the electrical signal flowing in each signal line 3 is connected to each signal line 3. The "detection" of the electrical signal in this embodiment refers to sampling of the electrical signal.

A scanning line driving circuit 104 which outputs the driving signal for turning on/off the TFT switch 4 to each scanning line 101 is connected to each scanning line 101. Although in FIG. 2, one signal detection circuit 105 and one scanning line driving circuit 104 are shown in a simplified form, for example, a plurality of signal detection circuits 105 and a plurality of scanning line driving circuits 104 are provided, and a predetermined number (for example, 256) signal lines 3 and a predetermined number (for example, 256) of scanning lines 101 are respectively connected thereto. For example, when 1024 signal lines 3 and 1024 scanning lines 101 are provided, four scanning line driving circuits 104 to each of which 256 scanning lines 101 are connected are provided, and four signal detection circuits 105 to each of which 256 signal lines 3 are connected are provided.

The signal detection circuit 105 has an internal amplification circuit 50 which amplifies an input electrical signal for each signal line 3. In the signal detection circuit 105, an electrical signal which is input from each signal line 3 is amplified by the amplification circuit 50 and converted to a digital signal by an A/D (analog/digital) conversion circuit 54.

The amplification circuit 50 is constituted by a charge amplifier circuit, and includes an amplifier 52, such as an operational amplifier, a capacitor C connected in parallel to the amplifier 52, and an electric charge reset switch SW1 connected in parallel to the amplifier 52.

In the amplification circuit 50, electric charge (electrical signal) is read by the TFT switch 4 of the pixel 20 in a state where the electric charge reset switch SW1 is in the off state, the electric charge read by the TFT switch 4 is stored in the capacitor C, and a voltage value which is output from the amplifier 52 increases in accordance with the amount of electric charge to be stored.

A control unit 106 applies an electric charge reset signal to the electric charge reset switch SW1 to control the on/off of the electric charge reset switch SW1. If the electric charge reset switch SW1 is placed in the on state, the input side and the output side of the amplifier 52 are short-circuited, and the electric charge of the capacitor C is discharged.

The A/D conversion circuit 54 has a function of converting an electrical signal as an analog signal input from the amplification circuit 50 to a digital signal in a state where an S/H (sample-and-hold) switch SW is in the on state. The A/D conversion circuit 54 sequentially outputs an electrical signal converted to a digital signal to the control unit 106.

The electrical signals output from all the amplification circuits 50 in the signal detection circuit 105 are input to the A/D conversion circuit 54 of this embodiment. That is, the signal detection circuit 105 of this embodiment includes the single A/D conversion circuit 54 regardless of the number of amplification circuits 50 (signal lines 3).

The control unit 106 is connected to the signal detection circuit 105 and the scanning line driving circuit 104. The control unit 106 of this embodiment has a function of performing predetermined processing, such as noise rejection, on a digital signal converted in the signal detection circuit 105, detecting the timing of starting irradiation of a radiation, outputting a control signal representing the timing of signal detection to the signal detection circuit 105 based on the detected timing, and outputting a control signal representing the timing of outputting a driving signal to the scanning line driving circuit 104.

The control unit 106 of this embodiment is constituted by a microcomputer, and includes a CPU (Central Processing Unit), a ROM, a RAM, and a nonvolatile storage unit constituted by a flash memory or the like. The control unit 106 executes a program stored in the ROM on the CPU to perform control for radiographing a radiological image.

The control unit 106 compares the current value of a current flowing in the bias line 25A detected by the current detector 120 with a threshold value for radiation detection set in advance, and detects the timing of starting irradiation of a radiation depending on whether or not the current value is equal to or greater than the threshold value. That is, the irradiation state of the radiation is detected based on change in the current value for radiation detection. In this embodiment, an irradiation detection unit has the current detector 120 and the control unit 106. If a radiation is irradiated onto the radiation detector 10 and electric charge is generated by the radiation detection element 103 of the pixel 20, a current flows in each bias line 25 in accordance with the generated electric charge (the amount of electric charge). For this reason, in this embodiment, the relationship between the current value flowing in the bias line 25A from among the bias lines 25 and the dose of radiation irradiated onto the radiation detector 10 is obtained in advance, and a current value for radiation detection which is used to detect the irradiation start timing is set in advance. If the electric charge (the amount of electric charge) generated by the radiation detection element 103 increases, since the current value of the current flowing in the bias line 25A increases, the current value of the current flowing in the bias line 25A increases with the increase in the dose of irradiated radiation.

The control unit 106 performs control such that, if the irradiation start timing is detected, the scanning line driving circuit 104 and the signal detection circuit 105 start radiographing of a radiological image, stores electric charge generated by the radiation detection element 103 of each pixel 20 for a predetermined period, when the predetermined period elapses, sequentially outputs an on signal to the scanning line 101 to read an electrical signal (image information) through the signal line 3 for each pixel 20, and generates a radiological image based on the image information.

In this embodiment, when generating a radiological image in the control unit 106, processing for complementing image information obtained from the pixel 20 (in FIG. 2, the pixel 20 connected to the signal line 3 (D3)), in which the radiation detection element 103 is connected to the bias line 25B, with image information obtained from the pixels 20 (in FIG. 2, the pixel 20 connected to the signal line 3 (D2) and the pixel 20 connected to the signal line 3 (D4)) in a column adjacent to the pixel 20, thereby generating a radiological image which is represented by the irradiated radiation. In the pixel 20 in which the radiation detection element 103 is connected to the bias line 25A, since the current detector 120 is a load (resistance), based on bias voltage V=current I×resistance R, the bias voltage fluctuates depending on the load (resistance) when electric charge flows. Since the dark current or gain of the radiation detection element 103 fluctuates with the bias voltage, in this embodiment, the offset and sensitivity of each pixel 20 connected to the bias line 25A fluctuate. For this reason, the fluctuation in the offset and sensitivity of each pixel 20 connected to the bias line 25A is complemented with the pixels 20 connected to the adjacent bias line 25B. Specifically, in the control unit 106 of this embodiment, image information of each pixel 20 connected to the signal line 3 (D3) is substituted with the average value of adjacent pixels 20 in the row direction (the pixels 20 connected to the signal line 3 (D2) and the pixels 20 connected to the signal line 3 (D4)) to generate a radiological image as image information with corrected fluctuation in the offset and sensitivity.

The current detector 120 has a function of detecting the current flowing in the bias line 25A. In this embodiment, the current detector 120 has a function of detecting the current value of the current flowing between the bias power source 110 and the pixel 20 (radiation detection element 103) in accordance with the irradiated radiation (the dose of radiation). The configuration or the like of the current detector 120 is not particularly limited insofar as the current detector 120 can detect the current flowing in the bias line 25A. In this embodiment, the current value detected by the current detector 120 is output to the control unit 106.

Figure 4:
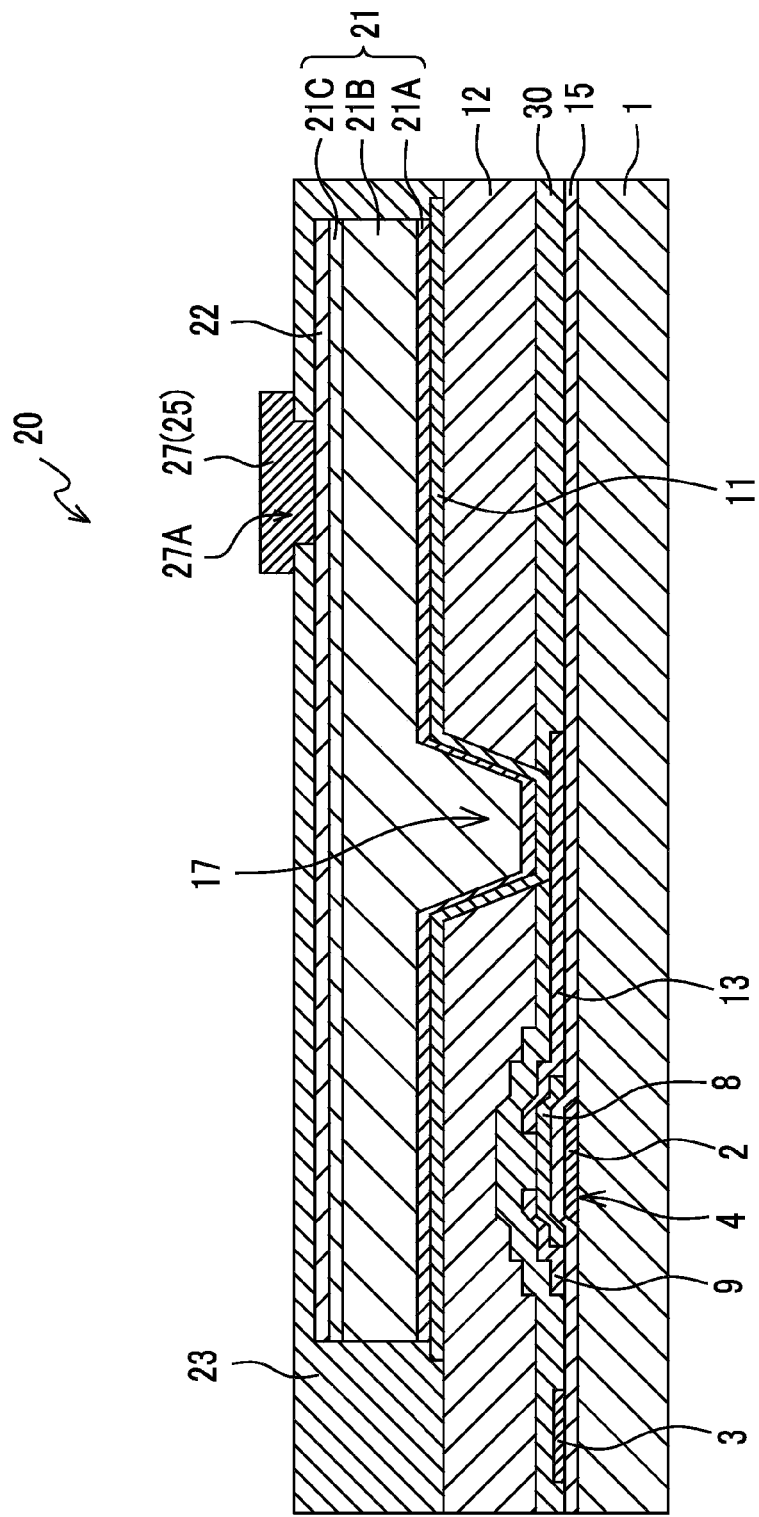
FIG. 4 is a linear sectional view of an example of the radiation detector according to the first embodiment.

FIG. 3 is a plan view showing the structure of the indirect conversion-type radiation detector 10 according to this embodiment. FIG. 4 is a sectional view showing the pixel 20 for radiological image radiographing taken along the line A-A of FIG. 3.

As shown in FIG. 4, in a pixel 20A of the radiation detector 10, a scanning line 101 (see FIG. 3) and a gate electrode 2 are formed on an insulating substrate 1 made of non-alkali glass or the like, and the scanning line 101 and the gate electrode 2 are connected together (see FIG. 3). Although a wiring layer (hereinafter, this wiring layer is referred to as "first signal wiring layer") in which the scanning line 101 and the gate electrode 2 are formed is formed of Al, Cu, or a laminated film mainly containing Al or Cu, the present invention is not limited thereto.

An insulating film 15 is formed on one surface of the first signal wiring layer, and a portion thereof on the gate electrode 2 acts as a gate insulating film in the TFT switch 4. The insulating film 15 is formed of, for example, $SiN_x$ or the like, and is formed by, for example, CVD (Chemical Vapor Deposition) formation.

A semiconductor active layer 8 is formed in an island shape on the gate electrode 2 on the insulating film 15. The semiconductor active layer 8 is the channel portion of the TFT switch 4, and is formed of, for example, an amorphous silicon film.

A source electrode 9 and a drain electrode 13 are formed in the overlying layer. In the wiring layer in which the source electrode 9 and the drain electrode 13, the signal line 3 is formed along with the source electrode 9 and the drain electrode 13. The source electrode 9 is connected to the signal line 3 (see FIG. 3). Although the wiring layer (hereinafter, referred to as "second signal wiring layer") in which the source electrode 9, the drain electrode 13, and the signal line 3 are formed is formed of Al, Cu, or a laminated film mainly containing Al or Cu, the present invention is not limited thereto. An impurity-doped semiconductor layer (not shown) is formed of impurity-doped amorphous silicon or the like between the source electrode 9 or the drain electrode 13 and the semiconductor active layer 8. These form the TFT switch 4 for switching. In the TFT switch 4, the source electrode 9 and the drain electrode 13 are reversed depending on the polarity of electric charge which is collected and stored by a lower electrode 11 described below.

A TFT protective layer 30 is substantially formed on the entire surface (entire region) of a region where the pixels 20 are provided on the substrate 1 to cover the second signal wiring layer, thereby protecting the TFT switch 4 or the signal line 3. The TFT protective layer 30 is formed of, for example, $SiN_x$ or the like, and is formed by, for example, CVD formation.

A coated insulating interlayer 12 is formed on the TFT protective layer 30. The insulating interlayer 12 is formed of a photosensitive organic material (for example, positive-type photosensitive acrylic resin: a material in which naphthoquinone diazido-based positive-type photosensitizer is mixed in a base polymer made of a copolymer of methacrylic acid and glycidyl methacrylate, or the like) having a low dielectric constant (relative dielectric constant $\in r=2$ to 4) to have a thickness of 1 to 4 μm.

In the radiation detector 10 of this embodiment, the insulating interlayer 12 suppresses capacitance between metals in the overlying layer and the underlying layer of the insulating interlayer 12 to be low. In general, this material has a function as a planarization film, and is effective for planarizing the step of the underlying layer. In the radiation detector 10 of this embodiment, a contact hole 17 is formed at a position where the insulating interlayer 12 and the drain electrode 13 of the TFT protective layer 30 face each other.

The lower electrode 11 of the radiation detection element 103 is formed on the insulating interlayer 12 so as to fill the contact hole 17 and to cover the pixel region, and the lower electrode 11 is connected to the drain electrode 13 of the TFT switch 4. The material for the lower electrode 11 is almost not limited insofar as the material is conductive when a semiconductor layer 21 described below has a thickness of about 1 μm. For this reason, if the lower electrode 11 is formed of an Al-based material or a conductive metal, such as ITO, there is no problem.

When the semiconductor layer 21 has a small thickness (about 0.2 to 0.5 μm), the absorption of light in the semiconductor layer 21 is not sufficient. For this reason, in order to prevent an increase in a leak current due to light irradiation onto the TFT switch 4, an alloy mainly containing a light-shielding metal or a laminated film is preferably used.

A semiconductor layer 21 which functions as a photodiode is formed on the lower electrode 11. In this embodiment, as the semiconductor layer 21, a PIN structure photodiode in which an n+ layer, an i layer, and a p+ layer (n+ amorphous silicon, amorphous silicon, and p+ amorphous silicon) are laminated is used. The semiconductor layer 21 is formed by laminating an n+ layer 21A, an i layer 21B, and a p+ layer 21C in order from the below. The i layer 21B generates electric charge (a pair of free electron and free hole) when light is irradiated. The n+ layer 21A and the p+ layer 21C function as a contact layer, and electrically connects the lower electrode 11 and an upper electrode 22 described below to the i layer 21B.

An upper electrode 22 is individually formed on each semiconductor layer 21. For the upper electrode 22, for example, a material having high transmittance, such as ITO or IZO (indium zinc oxide), is used. In the radiation detector 10 of this embodiment, the radiation detection element 103 includes the upper electrode 22 or the semiconductor layer 21, and the lower electrode 11.

A coated insulating interlayer 23 with an opening 27A corresponding to the upper electrode 22 is provided on the insulating interlayer 12, the semiconductor layer 21, and the upper electrode 22 so as to cover the semiconductor layer 21.

The bias line 25 (25A or 25B) is formed of Al, Cu, or an alloy or a laminated film mainly containing Al or Cu on the insulating interlayer 23. The bias line 25 (25A or 25B) has a contact pad 27 formed in the vicinity of the opening 27A, and is electrically connected to the upper electrode 22 through the opening 27A of the insulating interlayer 23.

A scintillator is provided on the surface of the radiation detector 10 formed in the above-described manner. For example, a protective film is formed of an insulating material having low light-absorption, and a scintillator made of GOS or the like is attached to the surface of the radiation detector 10 using adhesive resin having low light-absorption. For example, a scintillator made of CSI or the like is deposited directly on the surface of the radiation detector 10.

Figure 5:
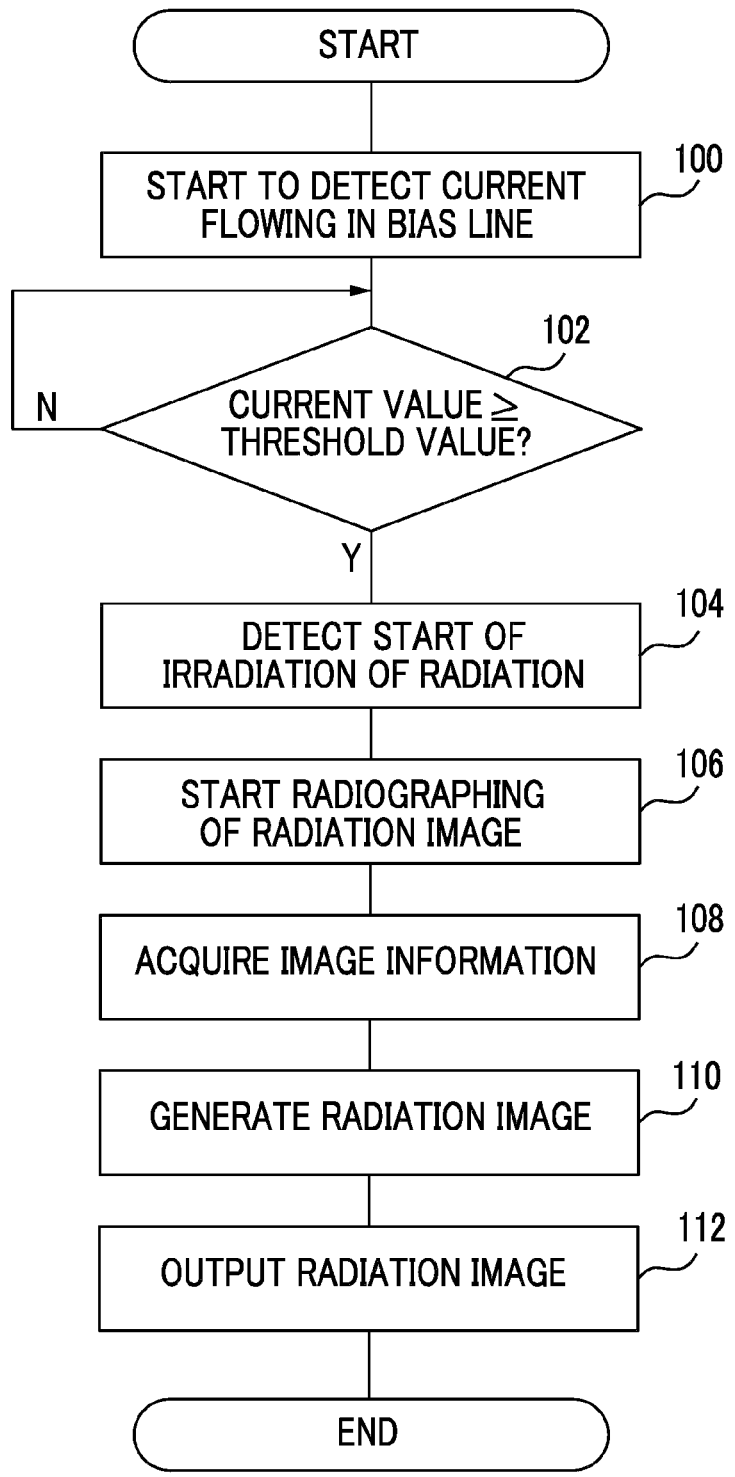
FIG. 5 is a flowchart of an example of processing which is performed in a control unit when radiographing a radiological image in the radiological image radiographing device according to the first embodiment.

Next, the flow of an operation when radiographing a radiological image using the radiological image radiographing device 100 configured as above will be described with reference to FIG. 5 focusing on a detection operation of irradiation start of a radiation. In this embodiment, a radiological image is radiographed based on an instruction from the control device 202 under the control of the control unit 106. In the control unit 106, if a radiographing instruction is received from the control device 202, a radiological image radiographing program is executed by the CPU, and thus the following processing is performed. FIG. 5 shows a flowchart of an example of the flow of the processing.

If the radiographing instruction is received, in Step 100, the current detector 120 starts the detection of the current flowing in the bias line 25A. In Step 102, the current value detected by the current detector 120 is compared with the threshold value for detecting the above-described irradiation start timing of the radiation to determine whether or not the detected current value is equal to or greater than the threshold value.

If radiation is irradiated from the irradiation device 204, the irradiated radiation is absorbed by the scintillator and converted to visible light. The radiation may be irradiated from either the front side or the rear side of the radiation detector 10. Light which is converted to visible light by the scintillator is irradiated onto the radiation detection element 103 of each pixel 20. In the radiation detection element 103, if light is irradiated, electric charge is generated. If the dose of irradiated radiation increases, the amount of electric charge which is generated by the radiation detection element 103 increases. With the increased amount of electric charge, a larger current flows in the bias line 25, and the current value which is detected by the current detector 120 increases. When the detected current value is smaller than the threshold value, it is determined that no radiation is yet irradiated, the determination result is negative, and a standby state is placed.

When the detected current value is equal to or greater than the threshold value, the determination result is positive, and the process progresses to Step 104. Then, the irradiation start timing of the radiation is detected, the process progresses to Step 106, and radiographing of a radiological image starts. Specifically, the control unit 106 instructs the radiation detector 10 to store electric charge. In the pixel 20 of the radiation detector 10, since the TFT switch 4 is still in the off state, and the state where electric charge is stored is placed.

In Step 108, image information of each pixel 20 is acquired. In this embodiment, it is determined whether or not a predetermined time elapses after the irradiation start is detected based on a timer (not shown), and when the predetermined time has elapsed, the electric charge storage in the pixel 20 ends, and the stored electric charge is read from each pixel 20. In regard to the reading of electric charge, specifically, if the on signal is sequentially applied to the gate electrode 2 of the TFT switch 4 through the scanning line 101, the TFT switch 4 of the pixel 20 is sequentially turned on, an electrical signal according to the amount of electric charge stored in each pixel 20 is output to the signal line 3, and the electric charge is read, thereby acquiring image information.

In Step 110, as described above, the image information of each pixel 20 connected to the bias line 25B is complemented with the average value of image information of the pixels 20 connected to the adjacent bias line 25A, and a radiological image is generated using the complemented image information. In Step 112, the generated radiological image is output to the control device 202, and then this processing ends.

As described above, in the radiological image radiographing device 100 of this embodiment, the bias lines 25 are provided for the respective columns of the pixels 20, and of a plurality of bias lines 25, the bias lines 25A provided at an interval of 10 mm are connected to the bias power source 110 through the current detector 120. The remaining bias lines 25B are connected directly to the bias power source 110 without passing through the current detector 120. In each pixel 20, if electric charge is generated by the radiation detection element 103 in accordance with the dose of irradiated radiation, a current flows in the bias line 25 in accordance with the generated current. The current detector 120 detects the current flowing in the bias line 25A, and the control unit 106 detects, as the timing of starting irradiation of a radiation, when the detected current (current value) is equal to or greater than the threshold value, and starts radiographing of a radiological image.

As described above, in this embodiment, only the bias lines 25A which are some of a plurality of bias lines 25 are connected to the current detector 120. The bias voltage fluctuates in each bias line 25A which is connected to the current detector 120 as a load (resistance), and in each pixel 20 connected to the bias line 25A, offset and sensitivity fluctuate. Since the bias lines 25B are connected directly to the bias power source 110 without passing through the current detector 120, there is fluctuation in the offset and sensitivity due to the fluctuation in the bias voltage. Accordingly, the region of the pixel 20 where there is no fluctuation in offset and sensitivity is obtained. That is, since a region where degradation of image quality does not occur is obtained, thereby suppressing the occurrence of, for example, image irregularity or the like and suppressing degradation of image quality of a radiological image.

In the radiological image radiographing device 100 of this embodiment, the control unit 106 complements the image information of each pixel 20 connected to the bias line 25A with the image information of each pixel 20 connected to the bias line 25B adjacent to the pixel 20, thereby further suppressing degradation of image quality of a radiological image.

Figure 15:
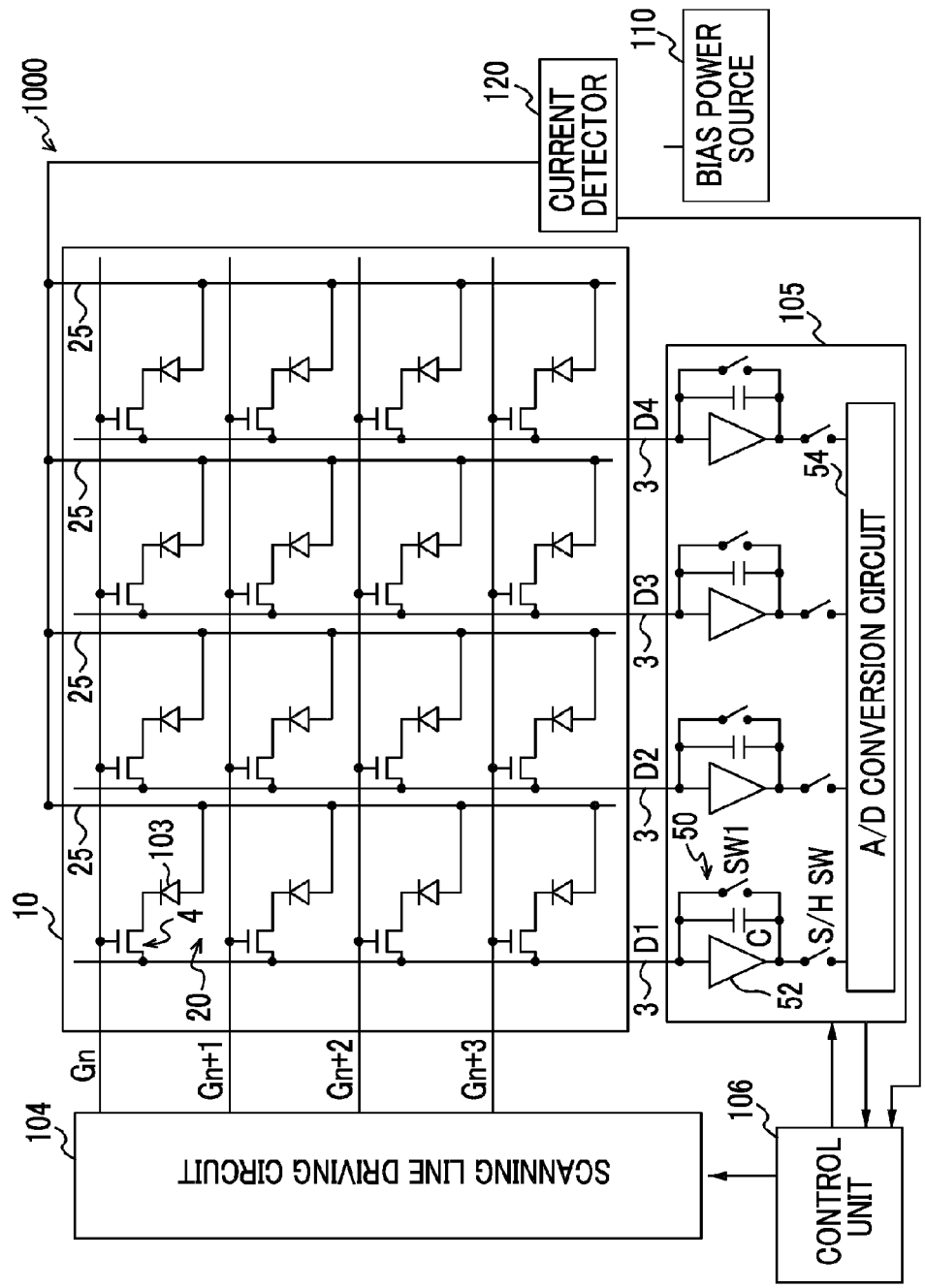
FIG. 15 is a configuration diagram showing an example of the overall configuration of a radiological image radiographing device of a comparative example.

As a comparative example, FIG. 15 shows a radiological image radiographing device 1000 in which all bias lines 25 are connected to the current detector 120. Since all bias lines 25 are connected to the current detector 120, in the control unit 106, the complement of image information in the control unit 106 of the radiological image radiographing device 100 of this embodiment is not performed. As described above, when all bias lines 25 are connected to the current detector 120, the bias voltage fluctuates in all of the bias lines 25 due to the load (resistance) of the current detector 120, and offset and sensitivity fluctuate in each pixel 20 due to the fluctuation in the bias voltage. As a result, artifact (image irregularity) occurs in the generated radiological image.

In the radiation detector 10 of this embodiment, as described above, it is possible to reduce the number of pixels 20 which are affected by the fluctuation in the bias voltage compared to the comparative example, and with the complement of image information, it is possible to suppress degradation of image quality of a radiological image, such that image irregularity or the like is made to be invisible.

Second Embodiment

Next, a second embodiment will be described.

A pixel 200 and a radiological image radiographing device 100 of this embodiment substantially have the same configuration and operation as in the first embodiment, thus, description of the same portions will not be repeated. In the radiological image radiographing device 100 of this embodiment, since the connection destination of the bias line 25A is different from the first embodiment, thus, different configuration and operation will be described.

Figure 6:
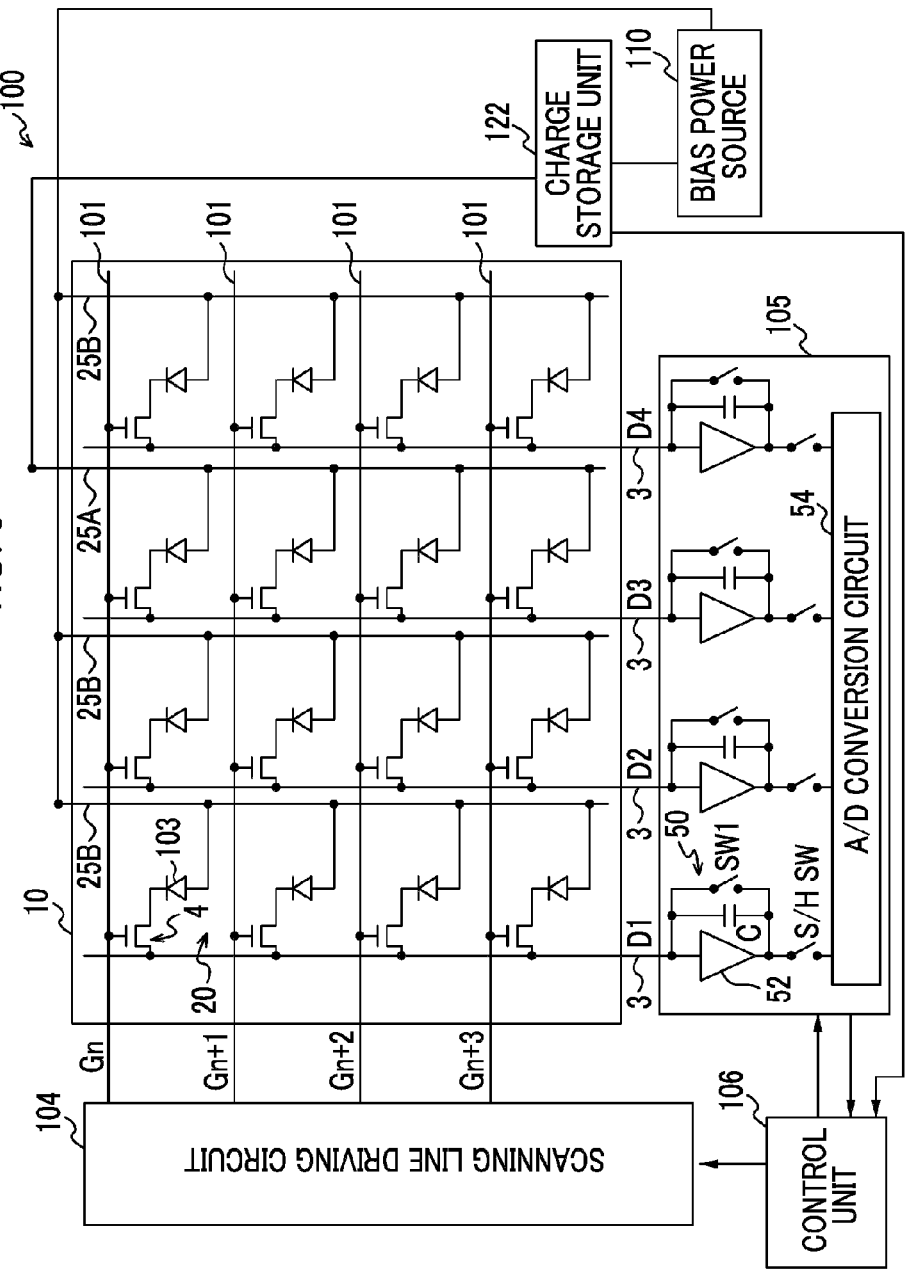
FIG. 6 is a configuration diagram showing an example of the overall configuration of a radiological image radiographing device according to a second embodiment.

FIG. 6 is a configuration diagram of an example of the overall configuration of the radiological image radiographing device 100 of this embodiment. As shown in FIG. 6, in the radiological image radiographing device 100 of this embodiment, the bias lines 25A are connected to an electric charge storage unit 122, and are connected to the bias power source 110 through the electric charge storage unit 122. The bias lines 25B are connected directly to the bias power source 110 without passing through the electric charge storage unit 122.

The electric charge storage unit 122 has a function of storing electric charge flowing in each bias line 25A for a predetermined time. In this embodiment, the electric charge storage unit 122 has a function of storing electric charge flowing between bias power source 110 and each pixel 20

(radiation detection element 103) for a predetermined time in accordance with the irradiated radiation (the dose of radiation). The configuration or the like of the electric charge storage unit 122 is not particularly limited insofar as the electric charge storage unit 122 can electric charge flowing in the bias line 25A for a predetermined time. In this embodiment, as a specific example, the electric charge storage unit 122 is constituted by a charge amplifier (not shown).

Figure 7:
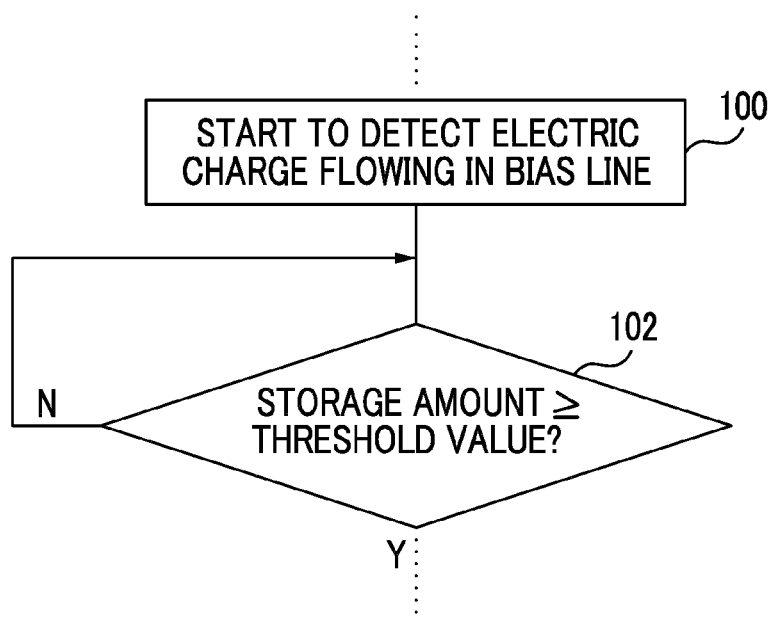
FIG. 7 is a flowchart of an example of processing which is performed in a control unit when radiographing a radiological image in the radiological image radiographing device according to the second embodiment.

Processing which is performed by the control unit 106 of this embodiment is substantially the same as the processing (see FIG. 5) of the first embodiment, thus, only different portions will be described. In this embodiment, since only Steps 100 and 102 are different from the processing of the first embodiment shown in FIG. 5, thus, only different steps are shown in FIG. 7.

In this embodiment, in Step 100, the control unit 106 detects the amount of electric charge stored by the electric charge storage unit 122. In Step 102, the control unit 106 compares the detected amount of electric charge with a threshold value for radiation detection set in advance, and detects the timing of starting irradiation of a radiation depending on whether or not the amount of electric charge is equal to or greater than the threshold value. As described above, if a radiation is irradiated onto the radiation detector 10, electric charge flows in each bias line 25 in accordance with the electric charge (the amount of electric charge) generated in the 20. For this reason, in this embodiment, the relationship between the amount of electric charge flowing in each bias line 25A from among the bias lines 25 and the dose of radiation irradiated onto the radiation detector 10 is obtained in advance, and the amount of electric charge for radiation detection which is used to detect the irradiation start timing is set in advance as a threshold value. That is, the irradiation state of the radiation is detected based on change in the amount of stored electric charge. An irradiation detection unit in this embodiment has the electric charge storage unit 122 and the control unit 106. If the electric charge (the amount of electric charge) generated by the radiation detection element 103 increases, since the amount of electric charge flowing in the bias line 25A increases, the amount of electric charge flowing in the bias line 25A increases with the increase in the dose of irradiated radiation.

As described above, in this embodiment, since only the bias lines 25A which are some of the bias lines 25 are connected to the electric charge storage unit 122, it is possible to reduce the number of pixels 20 which are affected by the fluctuation in the bias voltage due to the electric charge storage unit 122 serving as a load (resistance). Accordingly, as in the first embodiment, it is possible to suppress fluctuation in the offset and sensitivity of the pixel 20 and to suppress degradation of image quality of a radiological image.

Third Embodiment

Next, a third embodiment will be described.

A pixel 200 and a radiological image radiographing device 100 of this embodiment substantially have the same configuration and operation as the first embodiment and the second embodiment, thus, description of the same portions will not be repeated. In the radiological image radiographing device 100 of this embodiment, since the connection destination of the bias line 25A is different from the first embodiment and the second embodiment, thus, different configuration and operation will be described.

Figure 8:
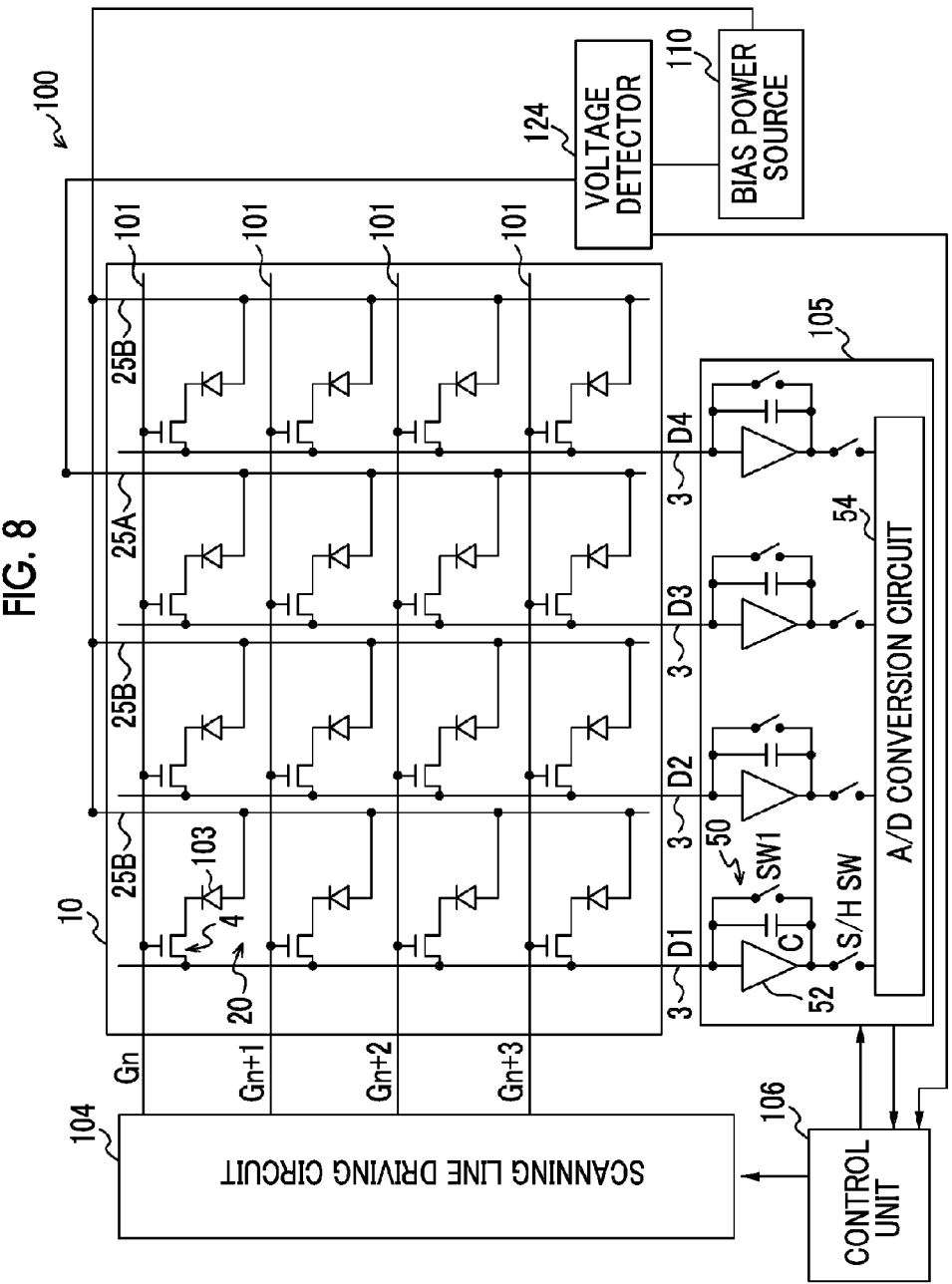
FIG. 8 is a configuration diagram showing an example of the overall configuration of the radiological image radiographing device according to a third embodiment.

FIG. 8 is a configuration diagram of an example of the overall configuration of the radiological image radiographing device 100 of this embodiment. As shown in FIG. 8, in the radiological image radiographing device 100 of this embodiment, the bias lines 25A are connected to a voltage detector 124, and are connected to the bias power source 110 through the voltage detector 124. The bias lines 25B are connected directly to the bias power source 110 without passing through the voltage detector 124.

The voltage detector 124 has a function of detecting a voltage of each bias line 25A. In this embodiment, the voltage detector 1240 has a function of detecting a voltage between the bias power source 110 and the pixel 20 (radiation detection element 103) in accordance with the irradiated radiation (the dose of radiation). The configuration or the like of the voltage detector 124 is not particularly limited insofar as the voltage detector 124 can detect a voltage of the bias line 25A. In this embodiment, a voltage value detected by the voltage detector 124 is output to the control unit 106.

Figure 9:
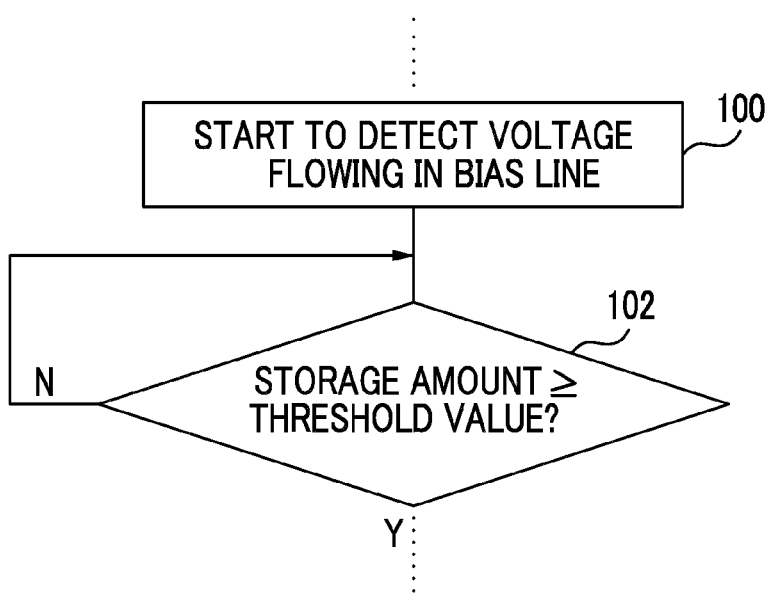
FIG. 9 is a flowchart of an example of processing which is performed in a control unit when radiographing a radiological image in the radiological image radiographing device according to the third embodiment.

Processing which is performed by the control unit 106 of this embodiment is substantially the same as the processing (see FIG. 5) of the first embodiment, thus, only different portions will be described. In this embodiment, since only Steps 100 and 102 are different from the processing of the first embodiment shown in FIG. 5, thus, only different steps are shown in FIG. 9.

In this embodiment, in Step 100, the control unit 106 starts to detect the voltage value of the bias line 25A detected by the voltage detector 124. In Step 102, the detected voltage value is compared with a threshold value for radiation detection set in advance, and the timing of starting irradiation of a radiation is detected depending on whether or not the voltage value is equal to or greater than the threshold value. That is, the irradiation state of the radiation is detected based on change in the detected voltage. If a radiation is irradiated onto the radiation detector 10 and electric charge is generated by the radiation detection element 103 of each pixel 20, a current flows in each bias line 25 and a voltage value changes in accordance with the generated electric charge (the amount of electric charge). For this reason, in this embodiment, the relationship between the voltage value of each bias line 25A from among the bias lines 25 and the dose of radiation irradiated onto the radiation detector 10 is obtained in advance, and a voltage value for radiation detection which is used to detect the irradiation start timing is set in advance. If the generated electric charge (the amount of electric charge) increases, since a current flowing in the bias line 25A increases and a voltage value increases, the voltage value of the bias line 25A increases with the increase in the dose of irradiated radiation. That is, an irradiation detection unit of this embodiment has the voltage detector 124 and the control unit 106.

As described above, in this embodiment, since only the bias lines 25A which are some of the bias lines 25 are connected to the voltage detector 124, it is possible to reduce the number of pixels 20 which are affected by the fluctuation in the bias voltage due to the voltage detector 124 serving as a load (resistance). Accordingly, as in the first embodiment and the second embodiment, it is possible to suppress fluctuation in the offset and sensitivity of the pixel 20 and to suppress degradation of image quality of a radiological image.

Fourth Embodiment

Next, a fourth embodiment will be described.

A pixel 200 and a radiological image radiographing device 100 of this embodiment substantially have the same configuration and operation as in the first embodiment, thus, description of the same portions will not be repeated. In the radiological image radiographing device 100 of this embodiment, the way to arrange the bias lines 25 (25A and 25B) is different from the first embodiment, thus, a different configuration will be described.

Figure 10:
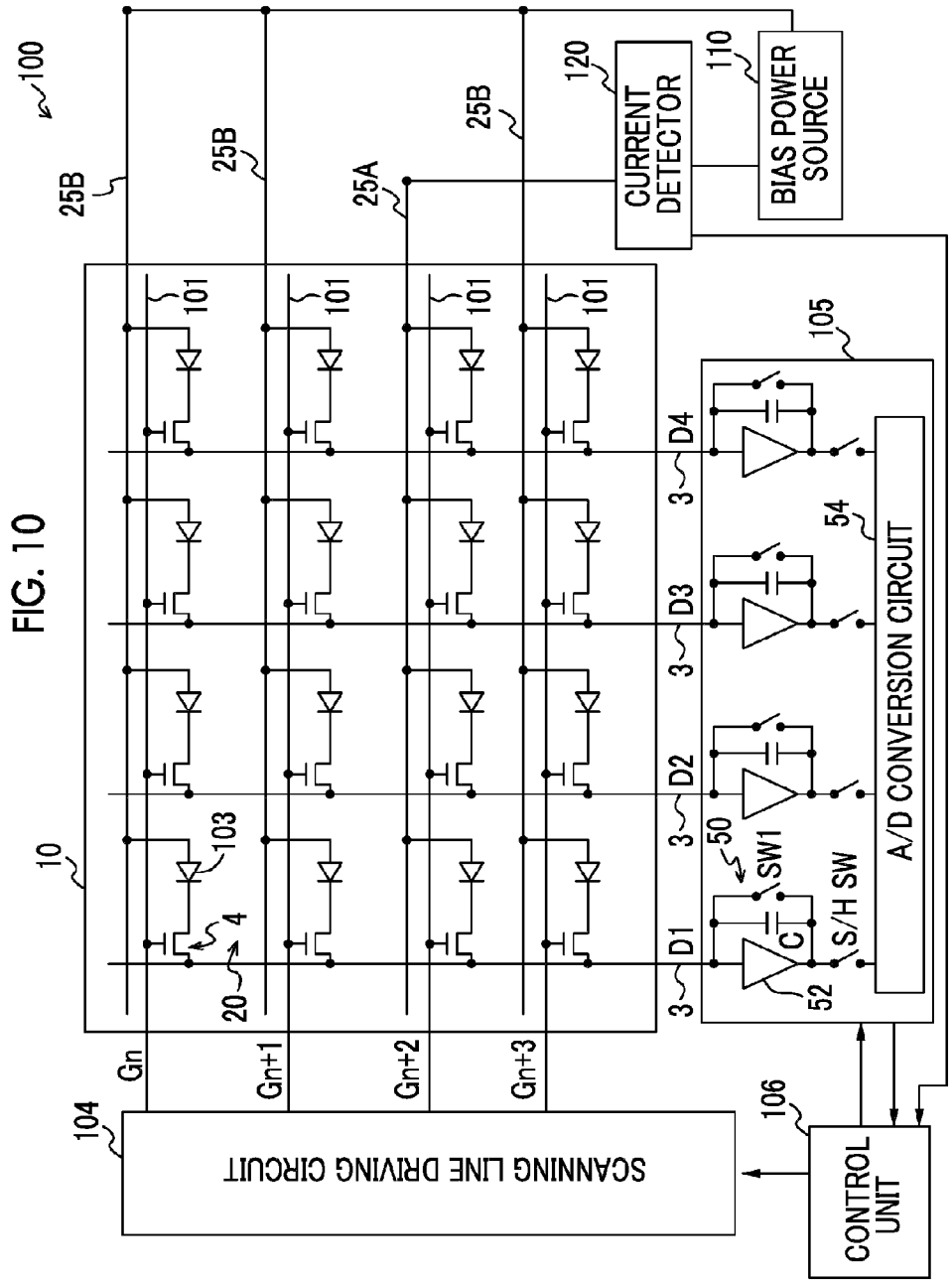
FIG. 10 is a configuration diagram showing an example of the overall configuration of the radiological image radiographing device according to a fourth embodiment.

FIG. 10 is a configuration diagram of an example of the overall configuration of the radiological image radiographing device 100 of this embodiment. As shown in FIG. 10, in the radiological image radiographing device 100 of this embodiment, bias lines 25 (25A and 25B) are substantially provided in parallel to the scanning lines 101 along the scanning lines 101 for the respective rows of the pixels 20.

In the radiological image radiographing device 100 of this embodiment, as described above, as a specific example, the pixel region of the radiation detector 10 has a size of 14 inches in the row direction and 17 inches in the column direction. In this way, when the length in the row direction is smaller than the length in the column direction, the bias lines 25 are substantially provided in parallel to the scanning lines 101 along the scanning lines 101 in the row direction of the pixels 20, it is possible to shorten the length (wiring length) of the bias lines 25 compared to a case where, as in the first embodiment (see FIG. 2), the bias lines are substantially provided in parallel to the signal lines 3 along the signal lines 3 in the column direction of the pixels 20.

As described above, in this embodiment, since the row direction of the radiation detector 10 is shorter than the column direction, the bias lines 25 are substantially provided in parallel to the scanning lines 101 along the scanning lines 101 for the respective rows of the pixels 20, thereby shortening the length (wiring length) of the bias lines 25. Accordingly, it is possible to decrease resistance, thereby suppressing fluctuation in the bias voltage which occurs in the bias lines 25A. Therefore, it is possible to suppress fluctuation in the offset and sensitivity of each pixel 20 connected to the bias line 25A and to suppress degradation of image quality of a radiological image.

Fifth Embodiment

Next, a fifth embodiment will be described.

A pixel 200 and a radiological image radiographing device 100 of this embodiment substantially have the same configuration and operation as in the first embodiment, thus, description of the same portions will not be repeated. In the radiological image radiographing device 100 of this embodiment, the way (the number of lines) to provide the bias lines 25A which are connected to the current detector 120 is different from the first embodiment, thus, a different configuration will be described.

Figure 11:
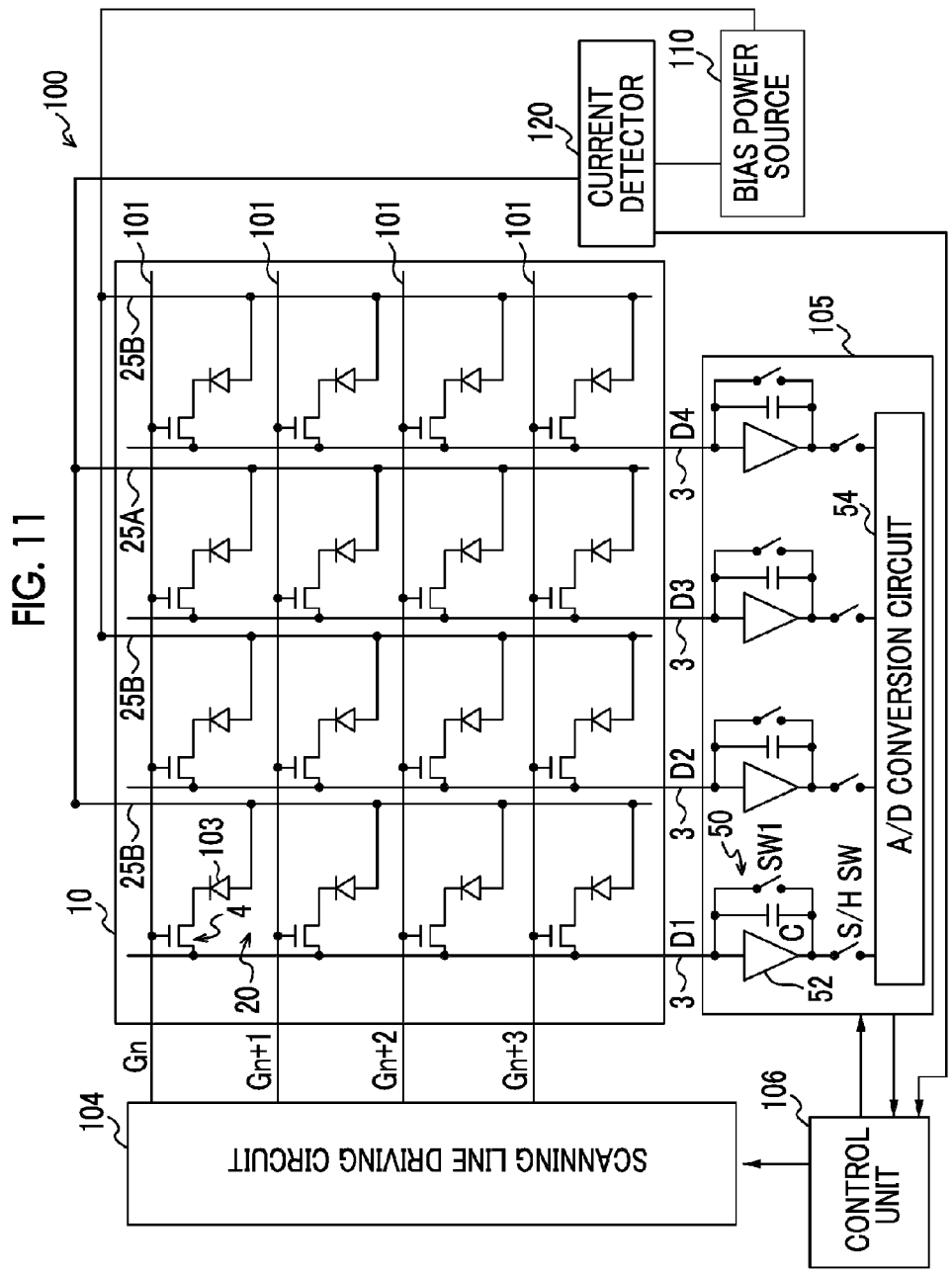
FIG. 11 is a configuration diagram showing an example of the overall configuration of the radiological image radiographing device according to a fifth embodiment.

FIG. 11 is a configuration diagram of an example of the overall configuration of the radiological image radiographing device 100 of this embodiment. As shown in FIG. 11, in the radiological image radiographing device 100 of this embodiment, the bias lines 25A from among the bias lines 25 are connected to the current detector 120 at an interval of one line, and are connected to the bias power source 110 through the current detector 120. That is, in the radiological image radiographing device 100 of this embodiment, bias lines 25A which are connected to the bias power source 110 through the current detector 120 and bias lines 25B which are connected directly to the bias power source 110 without passing through the current detector 120 are alternately provided.

As described above, in this embodiment, if the bias lines 25A from among the bias lines 25 are provided at an interval of one line, more bias lines 25A are connected to the current detector 120, and irradiation of a radiation can be detected for each smaller region, thereby improving detection accuracy of irradiation of a radiation (irradiation start timing).

Although in this embodiment, the bias lines 25A and the bias lines 25B are alternately provided one by one, for example, the bias lines 25A and the bias lines 25B may be alternately provided two by tow. When a plurality of adjacent lines are the bias lines 25A, since image information is hard to complement or image irregularity is easily viewed, it should suffice that the number of adjacent bias lines 25A is set in advance in accordance with the characteristic of the radiological image radiographing device 100 or desired image quality. The bias lines 25A from among the bias lines 25 may be provided at an interval of two lines. The interval is not particularly limited, and may be set in advance in accordance with radiation detection accuracy, desired image quality, or the like. The interval or the like of the bias lines 25A may differ depending on the arrangement position in the radiological image radiographing device 100.

From the viewpoint of improvement in image quality, it is preferable that the number of bias lines 25A is equal to or smaller than the number of bias lines 25B.

Sixth Embodiment

Next, a sixth embodiment will be described.

A pixel 200 and a radiological image radiographing device 100 of this embodiment substantially have the same configuration and operation as in the first embodiment, thus, description of the same portions will not be repeated. In the radiological image radiographing device 100 of this embodiment, since the way to read electric charge (image information) from the pixel 20 is different from the first embodiment, thus, different configuration and operation will be described.

Figure 12:
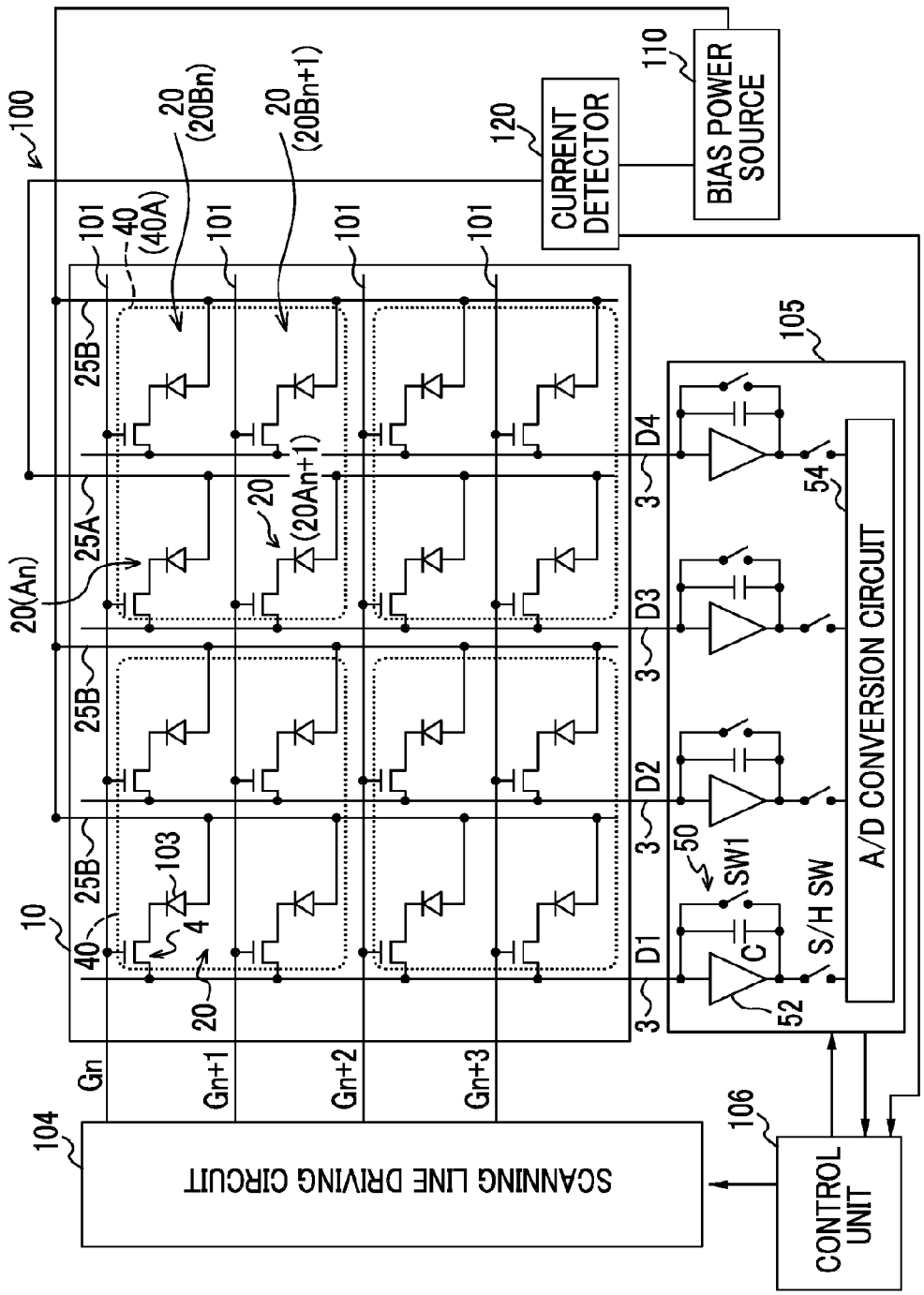
FIG. 12 is a configuration diagram showing an example of the overall configuration of the radiological image radiographing device according to a sixth embodiment.

FIG. 12 is a configuration diagram of an example of the overall configuration of the radiological image radiographing device 100 of this embodiment. As shown in FIG. 12, the overall configuration of the radiological image radiographing device 100 of this embodiment is the same as the radiological image radiographing device 100 (see FIG. 2) of the first embodiment.

In this embodiment, so-called binning for collectively acquiring, when 2 pixels×2 pixels are regarded as a single pixel 40 electric charge (image information) of four pixels 20 to read the electric charge (image information) is performed under the control of the control unit 106.

In this embodiment, as shown in FIG. 12, image information according to electric charge output from each pixel 20 connected to each bias line 25A and image information according to electric charge output from each pixel 20 connected to each bias line 25B are collected and acquired as single image information.

Specifically, the control unit 106 places the scanning lines 101 in the on state two by two using the scanning line driving circuit 104, and totals the electrical signals (image information) output from the signal lines 3 two by two. Thus, the result is acquired as image information of a pixel 40.

For example, in the case shown in FIG. 12, a scanning line 101 (Gn) and a scanning line 101 (Gn+1) are in the on state, an electrical signal (image information) obtained by totaling a pixel 20An and a pixel 20An+1 output to a signal line 3 (D3) and an electrical signal (image information) obtained by totaling a pixel 20Bn and a pixel 20Bn+1 output to a signal line 3 (D4) are totaled and acquired by the control unit 106 as image information of the pixel 40 (40A).

A radiological image may be generated with image information acquired through binning as the image information of the pixel 40, or a radiological image may be generated with image information of each pixel 20 acquired by collecting image information averaged by dividing collected image information by the number of pixels 20 (in FIG. 12, "4"). In the latter case, binning may be performed in a region where each pixel 20 connected to each bias line 25A is included. For example, in the case shown in FIG. 12, binning may not be performed on the pixels 20 which are connected to the signal line 3 (D1) and the signal line (D2).

As described above, image information according to electric charge output from the pixel 20 connected to the bias line 25A and image information according to electric charge output from the pixel 20 connected to the bias line 25B are totaled and acquired as single image information, thereby reducing fluctuation in image information due to fluctuation in the offset and sensitivity affected by the fluctuation in the bias voltage. For this reason, in the control unit 106 of this embodiment, it is not necessary to complement image information in the control unit 106 described in the first embodiment.

Although in this embodiment, so-called digital binning in which the electrical signals (image information) output to the signal lines 3 of adjacent pixels 20 in the row direction is performed, the present invention is not limited thereto. The radiation detector 10 is configured such that, in the pixels 20, electric charge is output to the same signal line 3, and so-called analog binning may be performed.

Seventh Embodiment

Next, a seventh embodiment will be described.

A pixel 200 and a radiological image radiographing device 100 of this embodiment substantially have the same configuration and operation as in the second embodiment, thus, description of the same portions will not be repeated. In the radiological image radiographing device 100 of this embodiment, since the way to read electric charge (image information) from the pixel 20 is different from the second embodiment, thus, different configuration and operation will be described.

Figure 13:
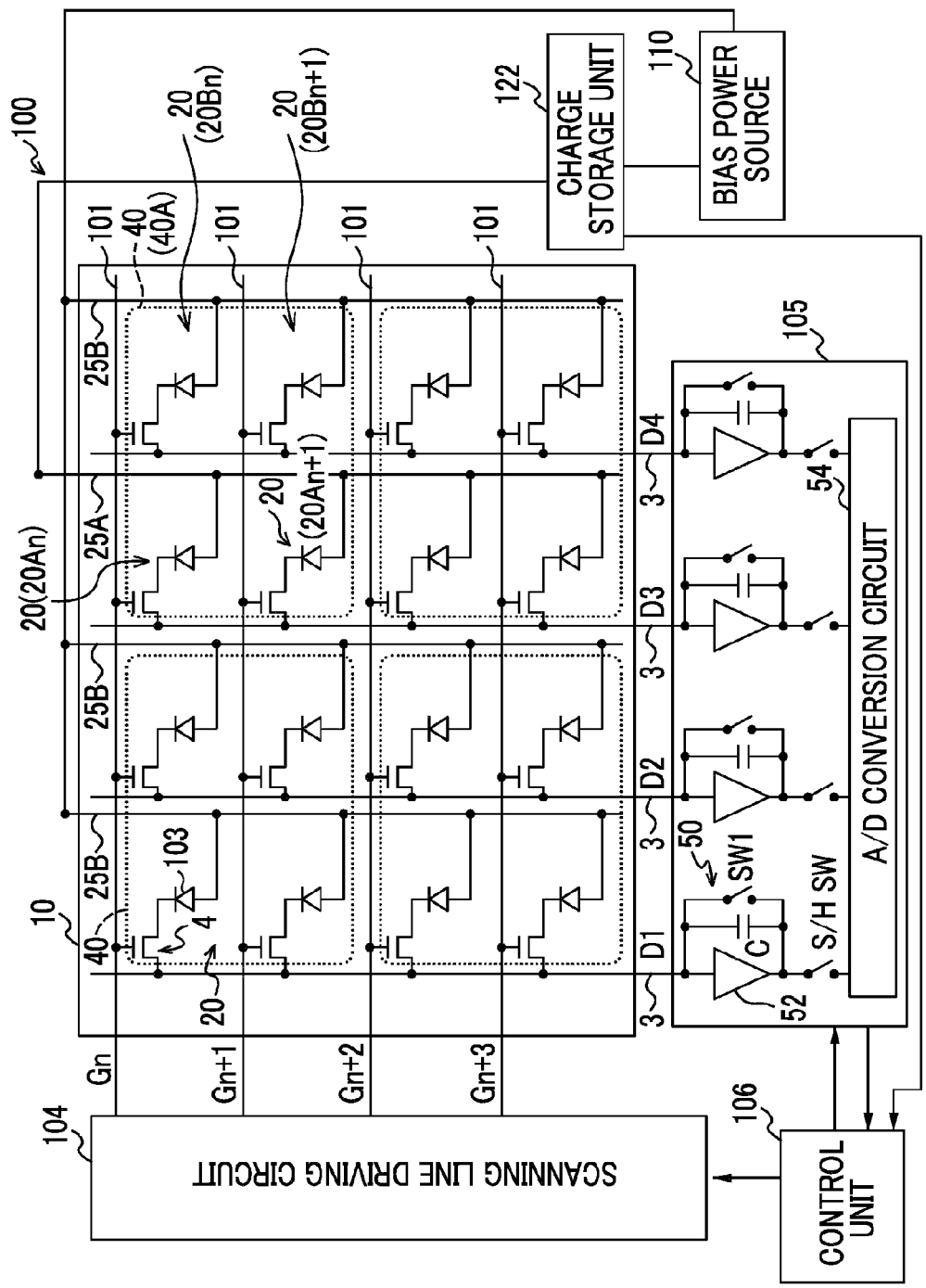
FIG. 13 is a configuration diagram showing an example of the overall configuration of the radiological image radiographing device according to a seventh embodiment.

FIG. 13 is a configuration diagram of an example of the overall configuration of the radiological image radiographing device 100 of this embodiment. As shown in FIG. 13, the overall configuration of the radiological image radiographing device 100 of this embodiment is the same as the radiological image radiographing device 100 (see FIG. 6) of the second embodiment.

In this embodiment, as in the sixth embodiment, so-called binning for collectively acquiring, when 2 pixels×2 pixels are regarded as a single pixel 40 electric charge (image information) of four pixels 20 to read the electric charge (image information) is performed under the control of the control unit 106.

In this embodiment, as shown in FIG. 13, image information according to electric charge output from each pixel 20 connected to each bias line 25A and image information according to electric charge output from each pixel 20 connected to each bias line 25B are collected and acquired as single image information.

Accordingly, in the radiological image radiographing device 100 of this embodiment, as in the sixth embodiment, image information according to electric charge output from the pixel 20 connected to the bias line 25A and image information according to electric charge output from the pixel 20 connected to the bias line 25B are totaled and acquired as single image information, thereby reducing fluctuation in image information due to fluctuation in the offset and sensitivity affected by the fluctuation in the bias voltage. For this reason, in the control unit 106 of this embodiment, it is not necessary to complement image information in the control unit 106 described in the first embodiment.

Eighth Embodiment

Next, an eighth embodiment will be described.

A pixel 200 and a radiological image radiographing device 100 of this embodiment substantially have the same configuration and operation as in the second embodiment, thus, description of the same portions will not be repeated. In the radiological image radiographing device 100 of this embodiment, since the way to read electric charge (image information) from the pixel 20 is different from the second embodiment, thus, different configuration and operation will be described.

Figure 14:
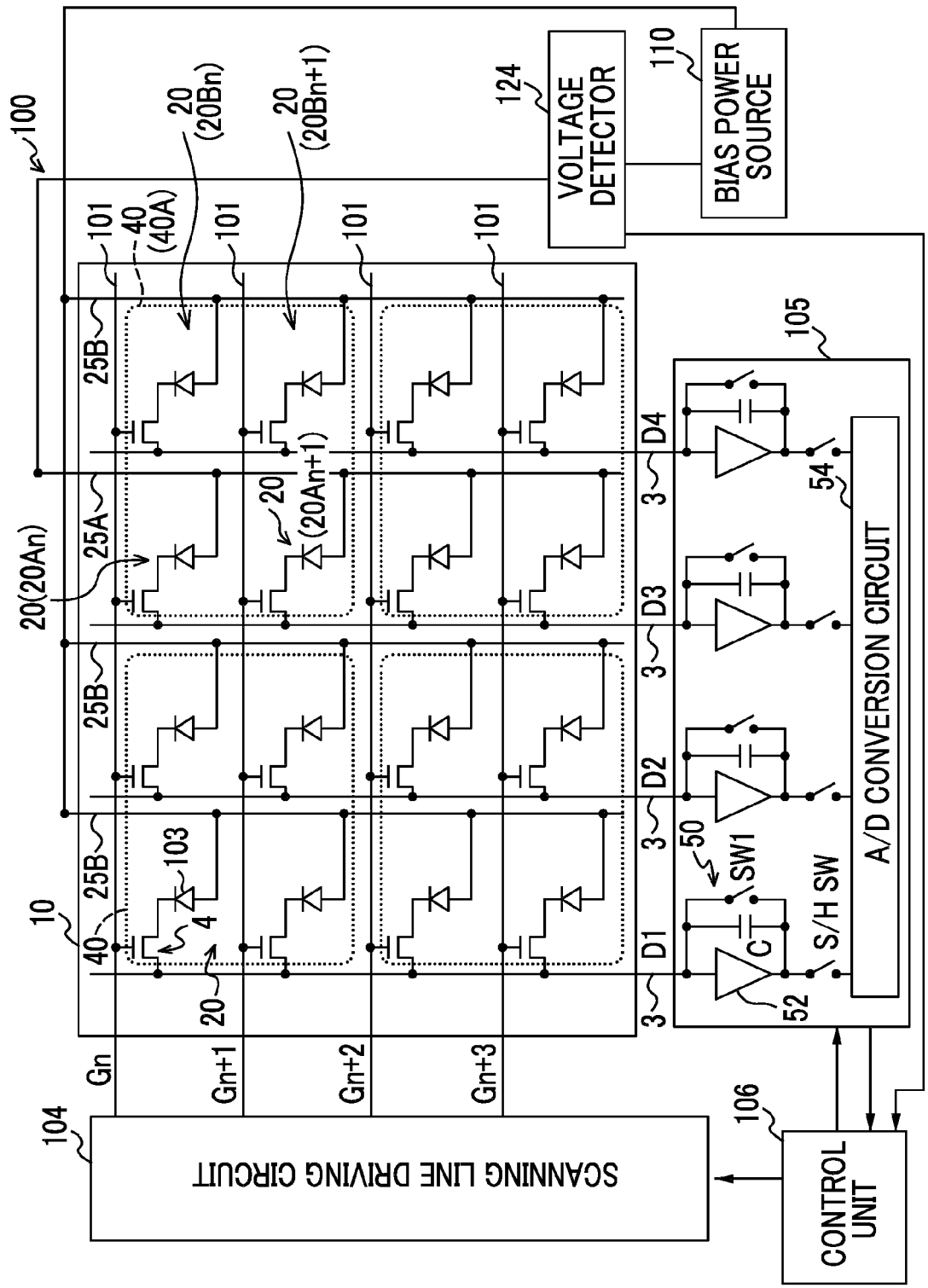
FIG. 14 is a configuration diagram showing an example of the overall configuration of the radiological image radiographing device according to an eighth embodiment.

FIG. 14 is a configuration diagram of an example of the overall configuration of the radiological image radiographing device 100 of this embodiment. As shown in FIG. 14, the overall configuration of the radiological image radiographing device 100 of this embodiment is the same as the radiological image radiographing device 100 (see FIG. 7) of the second embodiment.

In this embodiment, as in the sixth embodiment, so-called binning for collectively acquiring, when 2 pixels×2 pixels are regarded as a single pixel 40 electric charge (image information) of four pixels 20 to read the electric charge (image information) is performed under the control of the control unit 106.

In this embodiment, as shown in FIG. 14, image information according to electric charge output from each pixel 20 connected to each bias line 25A and image information according to electric charge output from each pixel 20 connected to each bias line 25B are collected and acquired as single image information.

Accordingly, in the radiological image radiographing device 100 of this embodiment, as in the sixth embodiment, image information according to electric charge output from the pixel 20 connected to the bias line 25A and image information according to electric charge output from the pixel 20 connected to the bias line 25B are totaled and acquired as single image information, thereby reducing fluctuation in image information due to fluctuation in the offset and sensitivity affected by the fluctuation in the bias voltage. For this reason, in the control unit 106 of this embodiment, it is not necessary to complement image information in the control unit 106 described in the first embodiment.

In the foregoing embodiments, which of the current value detected by the current detector 120, the amount of electric charge stored by the electric charge storage unit 122, and the voltage value detected by the voltage detector 124 is used when detecting a radiation (the irradiation start timing) is set depending on the characteristic (real time performance, sensitivity, or the like) in the radiation detector 10. When the dose of irradiated radiation is small and the absolute value of the fluctuation is small, while detection sensitivity is slightly deteriorated compared to a case where detection is performed based on the amount of stored electric charge, the real time performance (promptness) of fluctuation detection of the detection based on the current value and the voltage value is excellent. This is preferably applied when the real time performance is given priority. Meanwhile, when detection is performed based on the amount of stored electric charge, while the real time performance is slightly deteriorated compared to a case where detection is performed based on the current value or the voltage value, even when the absolute value of the fluctuation is small, detection sensitivity is excellent since the fluctuation can be integrated. This is preferably applied when detection sensitivity is given priority. These may be used in combination.

Although in the foregoing embodiments, the current value detected by the current detector 120, the amount of electric charge stored by the electric charge storage unit 122, or the voltage value detected by the voltage detector 124 is compared with the threshold value by the control unit 106 to detect the radiation (irradiation start timing), the present invention is not limited thereto. The current value, the amount of electric charge, or the voltage value may be compared with the threshold value by the current detector 120, the electric charge storage unit 122, or the voltage detector 124, and when the value is equal to or greater than the threshold value, a signal indicating this effect may be output to the control unit 106.

Although in the foregoing embodiments, a case where the control unit 106 of the radiological image radiographing device 100 detects the timing of starting the irradiation of the radiation has been described, the present invention is not limited thereto, and may be applied to when detecting the timing of stopping the irradiation of the radiation from the irradiation device 204, the timing at which a predetermined dose of radiation is irradiated, or the like.

Although in the foregoing embodiments, the indirect conversion type has been described, the present invention is not limited thereto, and may be applied to a direct conversion type in which a radiation is directly converted to electric charge by a semiconductor layer. In this case, a radiation detection element of a direct conversion type generates electric charge when a radiation is irradiated.

The configuration, operation, and the like of the radiological image radiographing device 100, the radiation detector 10, and the like described in the foregoing embodiments are just an example, and may be of course changed according to the situation without departing from the scope of the present invention.

Although in this embodiment, the radiation of the present invention is not particularly limited, X-ray, γ-ray, or the like may be applied.

What is claimed is:

1. A radiological image radiographing device comprising:
    a plurality of pixels arranged in a matrix, each pixel having a radiation detection element which generates electric charge according to the dose of irradiated radiation and a switch element which reads the electric charge generated by the radiation detection element and outputs the electric charge to a signal line;
    a plurality of bias lines which supply a bias voltage applied from a bias power source to the radiation detection elements of the plurality of pixels; and
    an irradiation detection unit which stores electric charge flowing in some bias lines from among the plurality of bias lines for a preset time and detects the irradiation state of the radiation based on change in the amount of stored electric charge.

2. The radiological image radiographing device according to claim 1,
    wherein at least one pixel adjacent to a pixel connected to a bias line which is used when detecting the irradiation of the radiation using the irradiation detection unit is connected to a bias line which is not used when detecting the irradiation of the radiation.

3. The radiological image radiographing device according to claim 1, further comprising:
    a complement unit which acquires image information according to the electric charge output from each of the plurality of pixels to the signal line for each pixel, and complements image information of a pixel connected to a bias line which is used when detecting the irradiation of the radiation using the irradiation detection unit with image information of a pixel adjacent to the pixel and connected to a bias line which is not used when detecting the irradiation of the radiation.

4. The radiological image radiographing device according to claim 1, further comprising:
    an acquisition unit which collectively acquires image information according to the electric charge output from a pixel connected to a bias line, which is used when detecting the irradiation of the radiation using the irradiation detection unit, to the signal line and image information according to the electric charge output from a pixel connected to a bias line, which is not used when detecting the irradiation of the radiation, to the signal line.

5. A radiological image radiographing method comprising:
    when radiographing a radiological image using the radiological image radiographing device according to claim 1,
    storing electric charge flowing in some bias lines from among a plurality of bias lines for a preset time;
    detecting the irradiation state of a radiation based on change in the amount of stored electric charge; and
    controlling radiographing of the radiological image based on the detected irradiation state.

6. A radiological image radiographing device comprising:
    a plurality of pixels arranged in a matrix, each pixel having a radiation detection element which generates electric charge according to the dose of irradiated radiation and a switch element which reads the electric charge generated by the radiation detection element and outputs the electric charge to a signal line;
    a plurality of bias lines which supply a bias voltage applied from a bias power source to the radiation detection elements of the plurality of pixels; and
    an irradiation detection unit which detects a current flowing in some bias lines from among the plurality of bias lines and detects the irradiation state of the radiation based on change in the detected current,
    wherein at least one pixel adjacent to a pixel connected to a bias line which is used when detecting the irradiation of the radiation using the irradiation detection unit is connected to a bias line which is not used when detecting the irradiation of the radiation.

7. A radiological image radiographing device comprising:
    a plurality of pixels arranged in a matrix, each pixel having a radiation detection element which generates electric charge according to the dose of irradiated radiation and a switch element which reads the electric charge generated by the radiation detection element and outputs the electric charge to a signal line;
    a plurality of bias lines which supply a bias voltage applied from a bias power source to the radiation detection elements of the plurality of pixels; and
    an irradiation detection unit which detects a voltage on some bias lines from among the plurality of bias lines and detects the irradiation state of the radiation based on change in the detected voltage,
    wherein at least one pixel adjacent to a pixel connected to a bias line which is used when detecting the irradiation of the radiation using the irradiation detection unit is connected to a bias line which is not used when detecting the irradiation of the radiation.

8. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a current flowing in some bias lines from among the plurality of bias lines and detects the irradiation state of the radiation based on change in the detected current,
wherein the number of bias lines which are used when detecting the irradiation of the radiation using the irradiation detection unit is equal to or smaller than the number of bias lines which are not used when detecting the irradiation of the radiation.

9. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a current flowing in some bias lines from among the plurality of bias lines and detects the irradiation state of the radiation based on change in the detected current,
wherein bias lines which are used when detecting the irradiation of the radiation using the irradiation detection unit are provided at an interval equal to or smaller than the width of the irradiation field of the radiation to be irradiated.

10. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a current flowing in some bias lines from among the plurality of bias lines and detects the irradiation state of the radiation based on change in the detected current,
further comprising:
a complement unit which acquires image information according to the electric charge output from each of the plurality of pixels to the signal line for each pixel, and complements image information of a pixel connected to a bias line which is used when detecting the irradiation of the radiation using the irradiation detection unit with image information of a pixel adjacent to the pixel and connected to a bias line which is not used when detecting the irradiation of the radiation.

11. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a voltage on some bias lines from among the plurality of bias lines and detects the irradiation state of the radiation based on change in the detected voltage,
further comprising:
a complement unit which acquires image information according to the electric charge output from each of the plurality of pixels to the signal line for each pixel, and complements image information of a pixel connected to a bias line which is used when detecting the irradiation of the radiation using the irradiation detection unit with image information of a pixel adjacent to the pixel and connected to a bias line which is not used when detecting the irradiation of the radiation.

12. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a current flowing in some bias lines from among the plurality of bias lines and detects the irradiation state of the radiation based on change in the detected current,
further comprising:
an acquisition unit which collectively acquires image information according to the electric charge output from a pixel connected to a bias line, which is used when detecting the irradiation of the radiation using the irradiation detection unit, to the signal line and image information according to the electric charge output from a pixel connected to a bias line, which is not used when detecting the irradiation of the radiation, to the signal line.

13. A radiological image radiographing device comprising:
a plurality of pixels arranged in a matrix, each pixel having a radiation detection element which generates electric charge according to the dose of irradiated radiation and a switch element which reads the electric charge generated by the radiation detection element and outputs the electric charge to a signal line;
a plurality of bias lines which supply a bias voltage applied from a bias power source to the radiation detection elements of the plurality of pixels; and
an irradiation detection unit which detects a voltage on some bias lines from among the plurality of bias lines and detects the irradiation state of the radiation based on change in the detected voltage,
further comprising:
an acquisition unit which collectively acquires image information according to the electric charge output from a pixel connected to a bias line, which is used when detecting the irradiation of the radiation using the irradiation detection unit, to the signal line and image information according to the electric charge output from a pixel connected to a bias line, which is not used when detecting the irradiation of the radiation, to the signal line.

14. A radiological image radiographing device comprising:
    a plurality of pixels arranged in a matrix, each pixel having a radiation detection element which generates electric charge according to the dose of irradiated radiation and a switch element which reads the electric charge generated by the radiation detection element and outputs the electric charge to a signal line;
    a plurality of bias lines which supply a bias voltage applied from a bias power source to the radiation detection elements of the plurality of pixels; and
    an irradiation detection unit which detects a current flowing in some bias lines from among the plurality of bias lines and detects the irradiation state of the radiation based on change in the detected current,
    wherein the bias lines are provided for the respective rows or columns of the pixels.

15. A radiological image radiographing system comprising:
    an irradiation device; and
    a radiological image radiographing device comprising:
    a plurality of pixels arranged in a matrix, each pixel having a radiation detection element which generates electric charge according to the dose of irradiated radiation and a switch element which reads the electric charge generated by the radiation detection element and outputs the electric charge to a signal line;
    a plurality of bias lines which supply a bias voltage applied from a bias power source to the radiation detection elements of the plurality of pixels; and
    an irradiation detection unit which detects a current flowing in some bias lines from among the plurality of bias lines and detects the irradiation state of the radiation based on change in the detected current,
    which radiographs a radiological image with a radiation irradiated from the irradiation device.

16. A radiological image radiographing method comprising:
    when radiographing a radiological image using a radiological image radiographing device comprising:
        a plurality of pixels arranged in a matrix, each pixel having a radiation detection element which generates electric charge according to the dose of irradiated radiation and a switch element which reads the electric charge generated by the radiation detection element and outputs the electric charge to a signal line;
        a plurality of bias lines which supply a bias voltage applied from a bias power source to the radiation detection elements of the plurality of pixels; and
        an irradiation detection unit which detects a current flowing in some bias lines from among the plurality of bias lines and detects the irradiation state of the radiation based on change in the detected current;
    detecting a current flowing in some bias lines from among a plurality of bias lines;
    detecting the irradiation state of a radiation based on change in the detected current; and
    controlling radiographing of the radiological image based on the detected irradiation state.

17. A radiological image radiographing method comprising:
    when radiographing a radiological image using a radiological image radiographing device comprising:
        a plurality of pixels arranged in a matrix, each pixel having a radiation detection element which generates electric charge according to the dose of irradiated radiation and a switch element which reads the electric charge generated by the radiation detection element and outputs the electric charge to a signal line;
        a plurality of bias lines which supply a bias voltage applied from a bias power source to the radiation detection elements of the plurality of pixels; and
        an irradiation detection unit which detects a voltage on some bias lines from among the plurality of bias lines and detects the irradiation state of the radiation based on change in the detected voltage;
    detecting a voltage on some bias lines from among a plurality of bias lines;
    detecting the irradiation state of a radiation based on change in the detected voltage; and
    controlling radiographing of the radiological image based on the detected irradiation state.

* * * * *